United States Patent
Steinmann

[11] Patent Number: 5,892,037
[45] Date of Patent: Apr. 6, 1999

[54] POLYMERIC ADDUCTS OF HINDERED AMINE-EPOXIDES AS STABILIZERS

[75] Inventor: Alfred Steinmann, Praroman, Switzerland

[73] Assignee: Ciba Specialty Chemicals Corporation, Tarrytown, N.Y.

[21] Appl. No.: 614,120

[22] Filed: Mar. 12, 1996

Related U.S. Application Data

[62] Division of Ser. No. 271,705, Jul. 7, 1994, Pat. No. 5,521,270.

[30] Foreign Application Priority Data

Jul. 13, 1993 [CH] Switzerland ............ 2098/93-4

[51] Int. Cl.$^6$ ............ C07D 241/02; C07D 241/04; C07D 215/00
[52] U.S. Cl. ............ 544/357; 544/358; 544/359; 544/360; 544/365; 544/374; 544/402; 546/16; 546/19; 546/20; 546/187; 546/189; 546/208; 546/216
[58] Field of Search ............ 546/16, 216, 19, 546/20, 187, 189, 208; 544/357, 358, 359, 360, 365, 374, 402

[56] References Cited

U.S. PATENT DOCUMENTS

| | | | |
|---|---|---|---|
| 4,210,612 | 7/1980 | Karrer et al. | 525/204 |
| 4,294,949 | 10/1981 | Karrer et al. | 526/263 |
| 4,413,096 | 11/1983 | Fu et al. | 525/204 |
| 4,499,220 | 2/1985 | Minagawa et al. | 526/263 |
| 4,894,399 | 1/1990 | Rody et al. | 524/91 |
| 5,047,489 | 9/1991 | Ravichanldran et al. | 526/263 |
| 5,274,016 | 12/1993 | Berner et al. | 524/100 |
| 5,541,274 | 7/1996 | Steinmann | 526/263 |

FOREIGN PATENT DOCUMENTS

| | | |
|---|---|---|
| 0001835 | 5/1979 | European Pat. Off. |
| 0526399 | 2/1993 | European Pat. Off. |

OTHER PUBLICATIONS

Luston & Voss, Macromol. Chem, Macromol Symp. 27, 231 (1989).

*Primary Examiner*—Kriellions S. Morgan
*Attorney, Agent, or Firm*—Luther A. R. Hall; David R. Crichton; Michele A. Kovaleski

[57] ABSTRACT

The invention relates to compounds obtainable by polymerization of esters or phenol ethers of the formula V

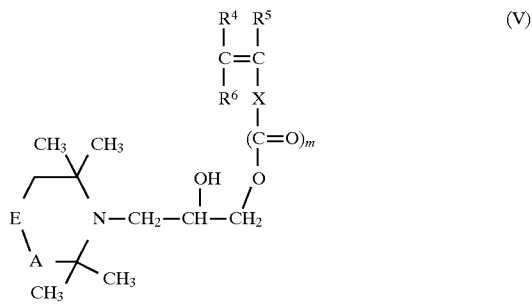

and/or of the formula VI

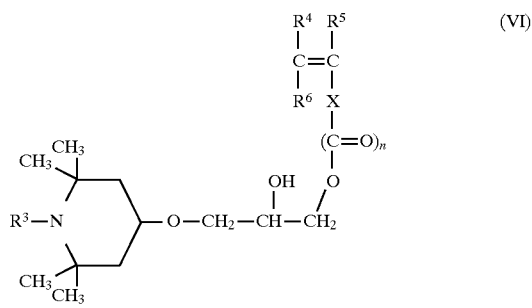

in which m and n are each 0 or 1, and A, E, $R^1$ to $R^6$ and X are as defined in claim 1, and up to 50 mol % of other, ethylenically unsaturated compounds. The homopolymers and copolymers according to the invention can advantageously be employed for the stabilization of organic polymers against the harmful effect of light, oxygen and/or heat.

1 Claim, No Drawings

POLYMERIC ADDUCTS OF HINDERED AMINE-EPOXIDES AS STABILIZERS

This is a divisional of Ser. No. 08/271,705, filed Jul. 7, 1994, now U.S. Pat. No. 5,521,220.

The invention relates to novel compounds which can be obtained by free-radical polymerization of ethylenically unsaturated 3-(2,2,6,6-tetramethylpiperidin-4-yloxy)- or 3-(2,2,6,6-tetramethylpiperidin-1-yl)-2-hydroxypropyl carboxylates or the corresponding vinylphenol ethers, to their use as stabilizers for organic material against the harmful effect of light, oxygen and/or heat, to novel monomeric starting materials, and to the corresponding stabilized compositions.

The preparation of some compounds of the 2,2,6,6-tetramethyl-4-(2,3-epoxypropoxy)piperidine type and their use as stabilizers for organic polymers is described, for example, by Luston and Vass, Makromol. Chem., Macromol. Symp. 27, 231 (1989).

The bonding of reactive polyalkylpiperidines of this type to fluoropolymers containing free carboxyl groups is described in EP-A-526 399.

EP-A-001 835 teaches the further reaction of the epoxy-containing piperidines with dicarboxylic anhydrides to give polyesters.

There continues to be a demand for novel polymeric light stabilizers having improved use properties and containing tetramethylpiperidine groups as side chains.

The invention therefore firstly relates to polymers containing tetramethylpiperidine side chains and comprising from 50 to 100 mol % of structural units of the formula I and/or II

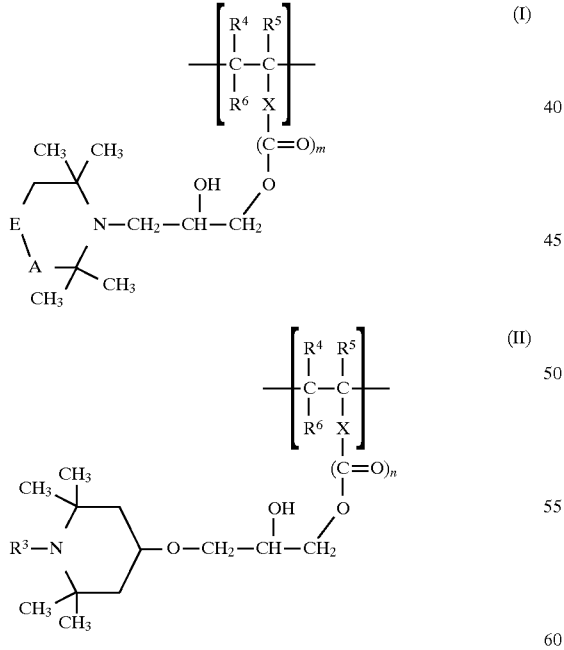

where the molecular weight $M_n$ of the homopolymer or copolymer, measured by gel permeation chromatography, is from 600 to 600,000 g/mol, and where k defined below is the number 2 or 3;
m and n, independently of one another, are 0 or 1;
A is —CH$_2$— or —CO—;

when A is methylene,

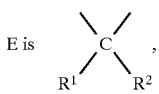

and
when A is carbonyl,

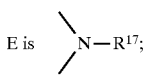

$R^1$ is hydrogen;
$R^2$ is hydrogen; —N(R$^{13}$)R$^{14}$; $C_1$–$C_{50}$alkoxy; $C_2$–$C_{50}$alkoxy which is interrupted by —O—, —S—, —CO—N(R$^{17}$)—, —N(R$^{17}$)—CO— or —NR$^{11}$— and/or by $C_5$–$C_8$cycloalkylene or phenylene and/or which contains 1 to 3 tertiary hydroxyl groups; $C_5$–$C_{12}$cycloalkoxy; $C_5$–$C_{12}$cycloalkoxy which is substituted by 1 to 4 —R$^{12}$ radicals; phenoxy; phenoxy which is substituted by 1 to 4 —R$^{12}$ radicals; or $C_7$–$C_{20}$aralkoxy; or
$R^1$ and $R^2$ together are an =O substituent; or together with the carbon atom to which they are bonded are a five- or six-membered ring of the formula

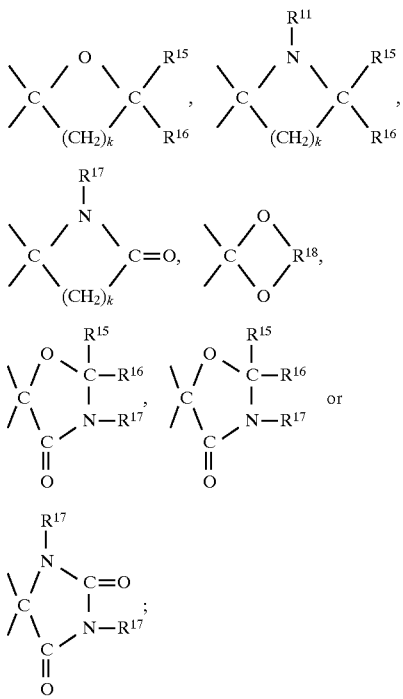

$R^3$ is hydrogen; $C_1$–$C_{36}$alkyl, $C_1$–$C_{36}$alkoxy, $C_7$–$C_{36}$aralkyl or $C_7$–$C_{36}$aralkoxy, each of which is unsubstituted or substituted by $C_5$–$C_8$cycloalkyl or —CO—N(R$^{17}$)$_2$ or is interrupted in the aliphatic part by $C_5$–$C_8$cycloalkylene, —CO—N(R$^{17}$)— or —N(R$^{17}$)—CO— or oxygen or sulfur or are substituted in the aromatic part by 1 to 3 $C_1$–$C_4$alkyl or $C_1$–$C_4$alkoxy radicals; $C_5$–$C_{12}$cycloalkyl which is unsubstituted or substituted by 1 to 3 $C_1$–$C_4$alkyl or $C_1$–$C_4$alkoxy radicals; $C_5$–$C_{12}$cycloalkoxy which is unsubstituted or substituted by 1 to 3 $C_1$–$C_4$alkyl or $C_1$–$C_4$alkoxy radicals; $C_6$–$C_{10}$aryl which is unsubstituted or substituted by 1 to 3 $C_1$–$C_4$alkyl or $C_1$–$C_4$alkoxy radicals; $C_6$–$C_{10}$aryloxy which is unsubstituted or substituted by 1 to 3 $C_1$–$C_4$alkyl or $C_1$–$C_4$alkoxy radicals; —CO—$R^{11}$; or benzoyl or naphthoyl, each of which is substituted by $C_1$–$C_4$alkyl;

$R^4$ and $R^5$, independently of one another, are hydrogen; $C_1$–$C_{18}$alkyl; phenyl; or $C_7$–$C_9$phenylalkyl; or one of $R^4$ or $R^5$ is additionally chlorine;

$R^6$ has one of the meanings given for $R^4$ and $R^5$ apart from chlorine; or is a direct bond to the group X; or is a group of the formula —X—(CO)$_m$—$Z^4$ or —X—(CO)$_n$—$Z^5$;

$R^{11}$ is $C_1$–$C_{18}$alkyl; $C_5$–$C_7$cycloalkyl; phenyl; naphthyl; $C_7$–$C_9$phenylalkyl; or $C_{11}$–$C_{14}$naphthylalkyl;

$R^{12}$ is $C_1$–$C_{18}$alkyl; $C_5$–$C_7$cycloalkyl; phenyl or benzyl;

$R^{13}$ and $R^{14}$, independently of one another, are $C_1$–$C_{50}$alkyl; or $C_2$–$C_{50}$alkyl which is interrupted by —O—, —S—, —CO—N($R^{17}$)—, —N($R^{17}$)—CO— or —N$R^{11}$— and/or by $C_5$–$C_8$cycloalkylene or phenylene and/or contains 1 to 3 tertiary hydroxyl groups; or $C_5$–$C_{12}$cycloalkyl which is unsubstituted or substituted by 1 to 4 —$R^{12}$ radicals; phenyl which is unsubstituted or substituted by 1 to 4 —$R^{12}$ radicals; or $C_7$–$C_{20}$aralkyl; or $R^{13}$ and $R^{14}$, together with the nitrogen atom to which they are bonded, are a cyclic imide of the formula

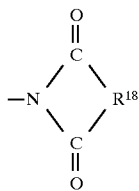

whose ring structure contains 4 to 6 carbon atoms;

$R^{15}$ and $R^{16}$, independently of one another, are H; or $C_1$–$C_{12}$alkyl; or together are straight-chain, α,ω-linked $C_4$–$C_{13}$alkylene;

$R^{17}$ is hydrogen or has one of the meanings of $R^{11}$;

$R^{18}$ is $C_2$–$C_{18}$alkylene;

X, in the case where $R^6$ is a direct bond to the group X, is the trivalent group

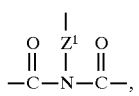

where the free valencies localized on the two carbonyl groups bond to the adjacent carbon atoms of the polymer chain;

and X, when $R^6$ is not a direct bond to the group X and in the case where m=0 or n=0, is phenylene or phenylene which is substituted by —$Z^4$ or —$Z^5$;

and X, when $R^6$ is not a direct bond to the group X and in the case where m=1 or n=1, is a direct bond; $C_1$–$C_4$alkylene; phenylene; or —$Z^2$-$Z^3$—, where $Z^2$ bonds to the carbon atom of the polymer chain;

$Z^1$ is phenylene;

$Z^2$ is —O— or phenylene;

$Z^3$ is $C_1$–$C_8$alkylene;

$Z^4$ is a group of the formula Ia

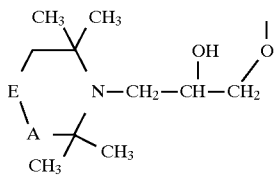

and $Z^5$ is a group of the formula IIa

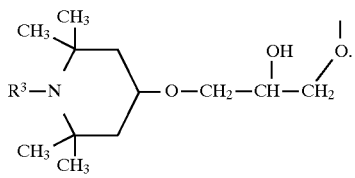

A tertiary hydroxyl group is taken to mean a substituent of the —OH type on a tertiary carbon atom. This is distinguished by the fact that it bonds to three further carbon atoms through its remaining three free valencies; the resulting compounds are also known as tertiary alcohols (cf. Beyer/Walter, Lehrbuch der Organischen Chemie [Textbook of Organic Chemistry], 20th Edition, pp. 59 and 111, S. Hirzel Verlag, Stuttgart 1984). A radical containing a tertiary hydroxyl group therefore contains at least 4 carbon atoms. Aryl stands for an aromatic hydrocarbon residue such as, for example, phenyl or naphthyl. Aralkyl means alkyl which is substituted by an aromatic hydrocarbon residue, e.g. a hydrocarbon residue having 6 to 10 carbon atoms; examples for aralkyl include benzyl and α-methylbenzyl.

If $R^2$, $R^3$, $R^{13}$ or $R^{14}$, within the scope of their stated meanings, contain alkyl or alkylene which is interrupted by —O—, —S—, —CO—N($R^{17}$)—, —N($R^{17}$)CO— or —N($R^{11}$)—, the alkyl or alkylene has at least 2 carbon atoms, preferably at least 4 carbon atoms, and is preferably interrupted by 1–6 —O— or —S— groups, in particular by 1–6 —O— groups; the heteroatoms or carbonyl groups preferably bond to saturated carbon atoms and not to other heteroatoms or carbonyl groups, and there are generally no peroxo or hydrazine structures. These radicals are particularly preferably polyoxyethylene chains whose ends are saturated by $C_1$–$C_8$alkyl radicals.

$R_2$ is particularly preferably a long chain radical or part of such a radical, for example a radical containing 5 to 50 carbon atoms, in particular 8 to 30 carbon atoms.

In the above formulae of substituents, for example the formulae Ia and IIa, free valencies are represented by dashes. For example, the subformula

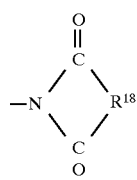

shows a possible meaning of the substituent $R^2$, and the horizontal dash represents the bond to the carbon atom in the 4-position in the piperidine ring of the formula I or Ia; the subformula

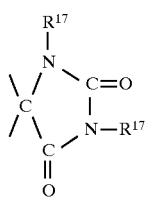

indicates possible joint meaning of the radicals R¹ and R², where the dashes represent bonds within the piperidine ring of the formula I or Ia, more precisely the bonds between the carbon atoms in the 3- and 4-positions and between the carbon atoms in the 4- and 5-position in the piperidine ring.

Two identical radicals in the same formula can have identical or different meanings; for example, one of the two $R^{17}$ radicals of the subformula $-CO-N(R^{17})_2$ can be hydrogen while the other $R^{17}$ radical has one of the meanings of $R^{11}$.

Novel polymers can comprise, for example, the following recurring units:

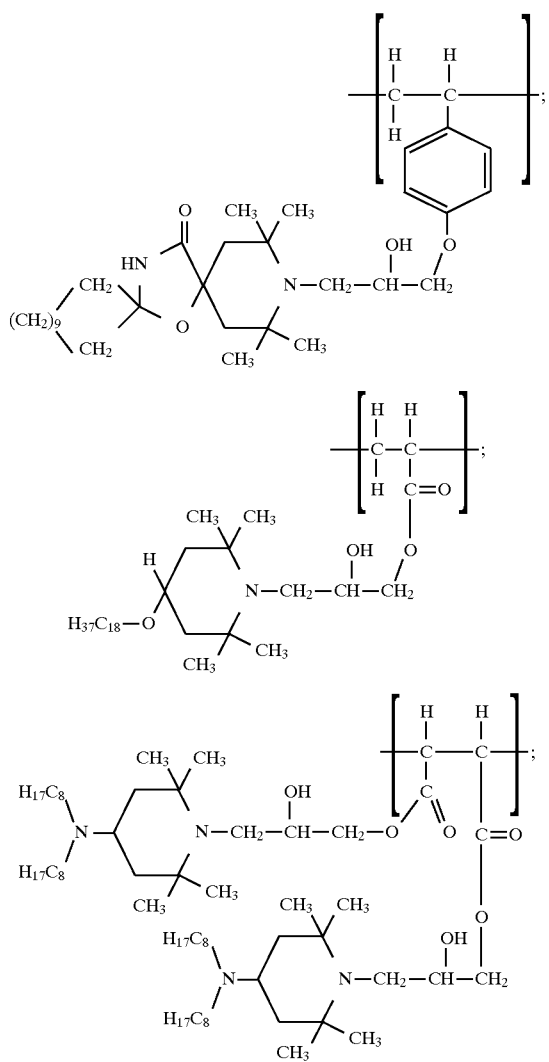

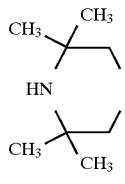

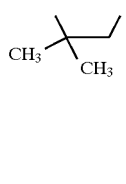

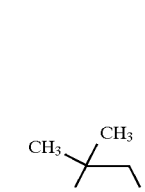

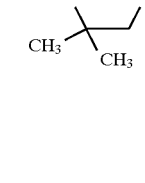

Said homopolymers and copolymers can advantageously be employed for the stabilization of organic polymers against the harmful effect of light, oxygen and/or heat.

Alkyl $R^3$, $R^4$, $R^5$, $R^6$, $R^{11}$, $R^{12}$, $R^{13}$, $R^{14}$, $R^{15}$, $R^{16}$ and $R^{17}$ and $R^7$, $R^8$, $R^9$ and $R^{10}$ below can be, within the scope of the definitions given, branched or unbranched alkyl, such as methyl, ethyl, propyl, isopropyl, n-butyl, sec-butyl, isobutyl, t-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, octadecyl, eicosyl, docosyl, pentacosyl or triacosyl.

Examples of the meanings of $R^3$ include the following: branched or unbranched $C_1$–$C_{36}$alkyl such as methyl, ethyl, propyl, isopropyl, n-butyl, sec-butyl, isobutyl, t-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, octadecyl, eicosyl, docosyl, pentacosyl or triacosyl; preference is given to unbranched alkyl, particularly preferably unbranched $C_1$–$C_{18}$alkyl; branched or unbranched $C_1$–$C_{36}$alkoxy, in particular $C_6$–$C_{18}$alkoxy such as hexyloxy, heptyloxy, octyloxy, nonyloxy, decyloxy, undecyloxy or dodecyloxy; $C_5$–$C_8$cycloalkyl-substituted alkyl or alkoxy, such as cyclopentylmethyl, cyclohexylmethyl, cycloheptylmethyl, cyclooctylmethyl, cyclohexylethyl, 2-cyclohexyl-n-propyl, 3-cyclohexyl-n-propyl, 4-cyclohexyl-n-butyl; alkyl or alkoxy which is interrupted by $C_5$–$C_8$cycloalkylene or by 1 to 6 —O— groups, for example of the formulae

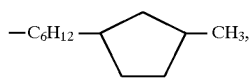

—$C_2H_4$—O—$C_2H_4$—O—$C_{12}H_{25}$, —$(C_2H_4$—O$)_4$—$C_4H_9$ or —$(C_2H_4$—O$)_6$—$C_4H_9$; $C_5$–$C_8$cycloalkyl or $C_5$–$C_8$cycloalkoxy which is unsubstituted or alkyl-substituted, such as cyclopentyl, cyclopentoxy, cyclohexyl, cyclohexyloxy, cycloheptyl, cycloheptyloxy, cyclooctyl, cyclooctyloxy, 2- or 4-methylcyclohexyloxy, dimethylcyclohexyloxy, trimethylcyclohexyl, t-butylcyclohexyl, in particular cyclohexyl and cyclohexyloxy; phenyl, phenoxy; phenyl or phenoxy which is substituted by $C_1$–$C_4$alkyl; $C_7$–$C_{12}$phenylalkyl or $C_7$–$C_{12}$phenylalkoxy, for example benzyl, benzoxy, phenethoxy, 3-phenylpropoxy, α-methylbenzyl, α-methylbenzoxy, α,α-dimethylbenzyl or α,α-dimethylbenzoxy.

A is preferably methylene and E is preferably a group of the formula

The invention preferably relates to a homopolymer or copolymer comprising from 50 to 100 mol % of structural units of the formula I and/or II and from 0 to 50 mol % of structural units of the formula III

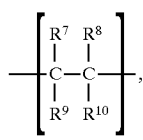

whose molecular weight $M_n$, measured by gel permeation chromatography, is from 1,000 to 300,000 g/mol, and in which $R^7$, $R^8$ and $R^9$, independently of one another, are hydrogen; —Cl; $C_1$–$C_{18}$alkyl; phenyl; phenyl which is substituted by 1 to 3 —Cl, $C_1$–$C_4$alkyl and/or $C_1$–$C_4$alkoxy radicals; or $C_7$–$C_9$phenylalkyl;

$R^{10}$ has one of the meanings given for $R^7$, $R^8$ and $R^9$; or is —CN; $C_1$–$C_{12}$alkoxycarbonyl; $C_1$–$C_{12}$alkanoyloxy; $C_1$–$C_{12}$alkoxy; or a group of the formula IVa or IVb

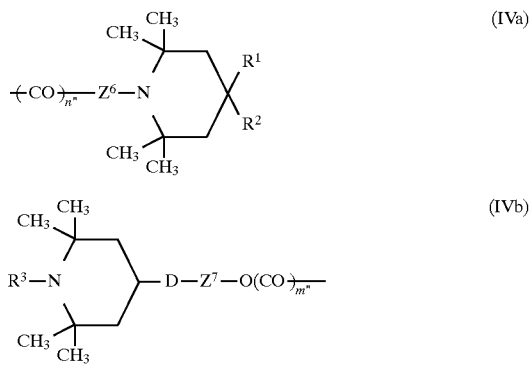

in which m" and n" are each the number 0 or the number 1;

D is —O— or —$NR^{11}$—;

$R^1$, $R^2$, $R^3$ and $R^{11}$ are as defined above;

$Z^6$ is a direct bond, $C_1$–$C_8$alkylene or polyoxyethylene of the formula —$CH_2$—$CH_2$—(O—$CH_2$—$CH_2$)$_h$—, where h is an integer in the range from 1 to 30; and $Z^7$ is $C_1$–$C_8$alkylene or polyoxyethylene of the formula —$CH_2$—$CH_2$—(O—$CH_2$—$CH_2$)$_h$—, where h is an integer in the range from 1 to 30.

The structural units of the formulae I, II and III shown above and below are generally constitutional repeating units. Copolymers can be, for example, random, alternating or block copolymers.

Preference is given to polymers consisting of recurring units of the formula I or II, or corresponding copolymers comprising 50 to 100 mol % of recurring units of the formula I and/or of the formula II. Polymers consisting of recurring units of the formula I or II are homopolymers or copolymers built up from 2 or more different units of the formula I or II; homopolymers are particularly preferred.

Particularly preferred copolymers comprising from 50 to 100 mol % of recurring units of the formula I and/or of the formula II are those whose other structural units conform to the formula III, in particular those built up from units of the formula I and III, or from units of the formula II and III (types A and B in the table below).

Some expedient compositions of the novel copolymers built up from units of the formulae I and/or II and III are shown in the table below:

| Type | Formula I | Formula II | remaining units |
|------|-----------|------------|-----------------|
| A | 50–95 mol % | none | Formula III |
| B | none | 50–95 mol % | Formula III |
| C | 1–30 mol % | 1–30 mol % | Formula III |
| D | 10–60 mol % | 10–60 mol % | Formula III |
| E | 40–80 mol % | 1–30 mol % | Formula III |
| F | 1–30 mol % | 40–80 mol % | Formula III |

The molecular weight $M_n$ of the homopolymer consisting of structural units of the formula I is preferably from 1,000 to 300,000 g/mol, the molecular weight $M_n$ of the homopolymer consisting of structural units of the formula II is preferably from 1,000 to 50,000 g/mol and the molecular weight $M_n$ of the copolymer is preferably from 1,000 to 100,000 g/mol.

Particular preference is given to homopolymers consisting of structural units of the formula I whose molecular weight $M_n$ is from 10,000 to 300,0000 g/mol, or homopolymers consisting of structural units of the formula II whose molecular weight $M_n$ is from 1,000 to 30,000 g/mol, in particular from 1,000 to 10,000 g/mol, or said copolymers whose molecular weight $M_n$ is from 3,000 to 100,000 g/mol.

Of particular interest is a homopolymer or copolymer comprising from 50 to 100 mol % of structural units of the formula I and/or II in which A is methylene and E is a group of the formula

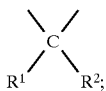

$R^1$ is hydrogen;

$R^2$ is hydrogen; —N($R^{13}$)$R^{14}$; $C_1$–$C_{18}$alkoxy; $C_4$–$C_{36}$alkoxy, which is interrupted by —CO—N($R^{17}$)— or —N($R^{17}$)—CO—; $C_5$–$C_8$cycloalkoxy, which is unsubstituted or substituted by —$R^{12}$; phenoxy, which is unsubstituted or substituted by 1 to 4 —$R^{12}$ radicals; or $C_7$–$C_{12}$aralkoxy; or $R^1$ and $R^2$ together are an =O substituent or, together with the carbon atom to which they are bonded, are a five- or six-membered ring of the formula

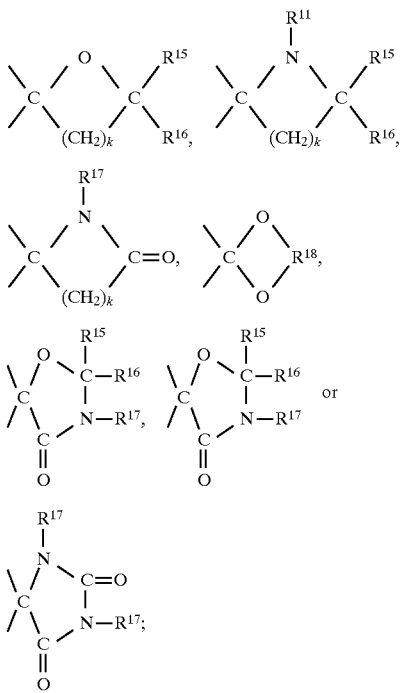

$R^3$ is $C_1$–$C_{36}$alkyl; $C_1$–$C_{36}$alkoxy; $C_5$–$C_{12}$cycloalkyl which is unsubstituted or substituted by 1 to 3 $C_1$–$C_4$alkyl or $C_1$–$C_4$alkoxy radicals; $C_5$–$C_{12}$cycloalkoxy which is unsubstituted or substituted by 1 to 3 $C_1$–$C_4$alkyl or $C_1$–$C_4$alkoxy radicals; phenyl which is unsubstituted or substituted by 1 to 3 $C_1$–$C_4$alkyl or $C_1$–$C_4$alkoxy radicals; naphthyl which is unsubstituted or substituted by 1 to 3 $C_1$–$C_4$alkyl or $C_1$–$C_4$alkoxy radicals; phenoxy which is unsubstituted or substituted by 1 to 3 $C_1$–$C_4$alkyl or $C_1$–$C_4$alkoxy radicals; naphthoxy which is unsubstituted or substituted by 1 to 3 $C_1$–$C_4$alkyl or $C_1$–$C_4$alkoxy radicals; $C_7$–$C_{12}$phenylalkyl which is unsubstituted or substituted on the phenyl ring by 1 to 3 $C_1$–$C_4$alkyl or $C_1$–$C_4$alkoxy radicals; $C_7$–$C_{12}$phenylalkoxy which is unsubstituted or substituted on the phenyl ring by 1 to 3 $C_1$–$C_4$alkyl or $C_1$–$C_4$alkoxy radicals; —CO—$R^{11}$; or benzoyl or naphthoyl, each of which is substituted by $C_1$–$C_4$alkyl;

$R^4$, $R^5$ and $R^6$, independently of one another, are hydrogen; $C_1$–$C_{18}$alkyl; phenyl; or $C_7$–$C_9$phenylalkyl; or one of $R^4$ and $R^5$ can alternatively be —Cl;

$R^{11}$ is $C_1$–$C_{18}$alkyl; $C_5$–$C_7$cycloalkyl; phenyl; or $C_7$–$C_9$phenylalkyl;

$R^{12}$ is $C_1$–$C_{18}$alkyl; $C_5$–$C_7$cycloalkyl; phenyl or benzyl;

$R^{13}$ and $R^{14}$, independently of one another, are $C_1$–$C_{18}$alkyl; $C_4$–$C_{36}$alkyl which is interrupted by —CO—N($R^{17}$)— or —N($R^{17}$)—CO—; $C_5$–$C_8$cycloalkyl which is unsubstituted or substituted by —$R^{12}$; phenyl which is unsubstituted or substituted by 1 to 4 —$R^{12}$ radicals; or $C_7$–$C_{12}$aralkyl;

$R^{15}$ and $R^{16}$, independently of one another, are H; or $C_1$–$C_{12}$alkyl; or together are straight-chain, α,ω-linked $C_4$–$C_{13}$alkylene;

$R^{17}$ is hydrogen or has one of the meanings of $R^{11}$;

X, in the case where m=0 or n=0, is phenylene or 1,3-phenylene which is substituted in the 5-position by —$Z^4$ or —$Z^5$;

X, in the case where m=1 or n=1, is a direct bond; $C_1$–$C_4$alkylene; phenylene; or —$Z^2$–$Z^3$—, where $Z^2$ bonds to the carbon atom of the polymer chain; and $Z^2$ to $Z^5$ are as defined above.

Particular preference is given to a homopolymer or copolymer comprising from 50 to 100 mol % of structural units of the formula I or II, in which A is methylene and E is a group of the formula

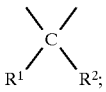

$R^2$ is —N($R^{13}$)$R^{14}$; or $C_2$–$C_{18}$alkoxy; $C_4$–$C_{36}$alkoxy, which is interrupted by —CO—N($R^{17}$)— or —N($R^{17}$)—CO—; or $C_7$–$C_{12}$aralkoxy; or $R_1$ and $R^2$ together are an =O substituent;

$R^3$ is $C_1$–$C_{12}$alkyl; $C_4$–$C_{18}$alkoxy; $C_5$–$C_8$cycloalkyl; $C_5$–$C_8$cycloalkoxy; $C_7$–$C_{12}$phenylalkyl; $C_7$–$C_{12}$phenylalkoxy; or —CO—$R^{11}$;

two of the radicals $R^4$, $R^5$ and $R^6$ are hydrogen and one is hydrogen; $C_1$–$C_4$alkyl; phenyl; or $C_7$–$C_9$phenylalkyl;

$R^{11}$ is $C_1$–$C_{18}$alkyl; cyclohexyl; phenyl; or $C_7$–$C_9$phenylalkyl;

$R^{13}$ and $R^{14}$, independently of one another, are $C_2$–$C_{18}$alkyl; $C_4$–$C_{36}$alkyl, which is interrupted by —CO—N($R^{17}$)— or —N($R^{17}$)—CO—; or $C_7$–$C_{12}$aralkyl;

$R^{17}$ is hydrogen or has one of the meanings of $R^{11}$;

X, in the case where m=0 or n=0, is phenylene; and

X, in the case where m=1 or n=1, is a direct bond; $C_1$–$C_4$alkylene or phenylene.

Particular emphasis should be placed on homopolymers or copolymers which comprise from 50 to 100 mol % of structural units of the formula I and/or II and in which A is methylene and E is a group of the formula

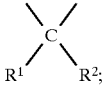

$R^2$ is $C_4$–$C_{18}$alkoxy; $C_4$–$C_{36}$alkoxy, which is interrupted by —CO—N($R^{17}$)— or —N($R^{17}$)—CO—; or $C_7$–$C_{12}$aralkoxy; or is —N($R^{13}$)$R^{14}$; or $R^1$ and $R^2$ together are an =O substituent;

$R^3$ is $C_1$–$C_6$alkyl; $C_4$–$C_{12}$alkoxy; cyclohexyl; cyclohexyloxy; benzyl; benzoxy; or benzoyl;

two of the radicals $R^4$, $R^5$ and $R^6$ are hydrogen and one is hydrogen; methyl; or phenyl;

$R^{13}$ and $R^{14}$, independently of one another, are $C_2$–$C_{12}$alkyl;

X, in the case where m=0 or n=0, is phenylene; and

X, in the case where m=1 or n=1, is a direct bond; or phenylene; in particular corresponding homopolymers.

Said homopolymers or copolymers are expediently prepared by subjecting a compound of the formula V

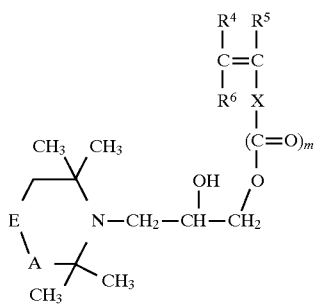

or a compound of the formula VI

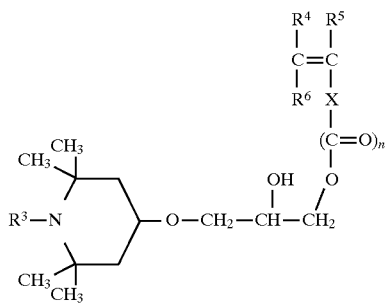

in which A, E, $R^1$, $R^2$, $R^3$, $R^4$, $R^5$, $R^6$, m, n and X are as defined above, or a mixture of compounds of the formulae V and VI;

or one or more compounds of the formulae V and VI together with up to 50 mol % of another free-radical-polymerizable compound, in particular a compound of the formula VIII

in which $R^7$, $R^8$, $R^9$ and $R^{10}$ are as defined above, to free-radical polymerization in a manner known per se. Polymers obtainable in this way comprise structural units of the formula I and/or II as described above and are a subject-matter of the invention.

The free-radical polymerization can be carried out using various techniques. These are described, for example, by S. Sandler and W. Karo in Polymer Synthesis, Vol. 1–3, Academic Press, New York 1968. The examples of conventional polymerization processes are bulk polymerization, solvent polymerization, emulsion polymerization, suspension polymerization and precipitation polymerization.

The polymerization is generally initiated by one of the conventional initiators for free-radical polymerization. These include thermal initiators, such as azo compounds, for example azoisobutyronitrile (AIBN), or peroxides, for example benzoyl peroxide, or redox initiator systems, such as a mixture of iron(III) acetylacetonate, benzoin and benzoyl peroxide, or photochemical free-radical formers, such as benzoin or benzil methyl ketal.

The initiator is expediently added to the reaction solution in an amount of 0.1–5 mol %, preferably 0.5–3 mol %, based on the amount of ethylenically unsaturated monomers.

In order to control the molecular weights, chain-transfer compounds can be added, for example in amounts of from 5 to 20 mol %. Examples of such compounds are disulfides, mercaptans, halides, butyl mercaptan, dibutyl sulfide, tetrachloromethane and others.

The polymerization is preferably carried out in solution. The reaction temperature is generally in a range from 10 to 200° C., preferably from 30 to 150° C., particularly preferably from 40 to 100° C.

Any solvents used must be inert under the reaction conditions. Suitable solvents include aromatic hydrocarbons, ketones and ethers. Examples thereof are benzene, toluene, xylene, ethylbenzene, isopropylbenzene, methyl ethyl ketone, acetone, cyclohexanone, diethyl ether, dibutyl ether, tetrahydrofuran and dioxane. Toluene and xylene are particularly preferred.

The polymerization is expediently carried out with exclusion of oxygen, for example under argon or nitrogen.

The starting compounds of the formula V are novel compounds which likewise represent a subject-matter of the invention. The starting compounds of the formula V are also already effective stabilizers for organic polymers for protection against damage by light, oxygen and/or heat.

The same applies to the starting compounds of the formula VI.

The starting compounds of the formulae V and VI are, in the case where m or n is 1, for example esters of the following acids: oleic acid, acrylic acid, methacrylic acid, maleic acid, fumaric acid, itaconic acid, glutaconic acid, mesaconic acid, dodeceylsuccinic acid, cinnamic acid, vinylbenzoic acid, allylbenzoic acid, maleimidobenzoic acid, stilbene-4,4'-dicarboxylic acid and vinylphenylacetic acid.

In the case where m or n is 0, the starting compounds of the formulae V and VI are phenol ethers derived, for example, from the following phenols: 2-, 3- or 4-vinylphenol; allylphenol, 4,4'-dihydroxystilbene; vinylresorcinol.

Since the starting compounds of the formulae V and VI are polymerizable stabilizers, the stabilization of a polymer can also be achieved by free-radical copolymerization or graft copolymerization with one or both compounds of the formulae V and VI. The invention therefore furthermore relates to a polymer protected against the harmful effect of light, oxygen and/or heat, which comprises from 0.01 to 5 mol % of structural units of the formula I and/or II.

A process for the preparation of a compound of the formula V starts from a piperidine compound of the formula Va

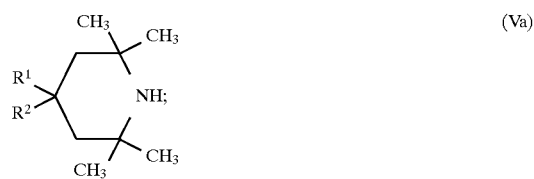

a process for the preparation of a compound of the formula VI starts from a piperidine compound of the formula VIa

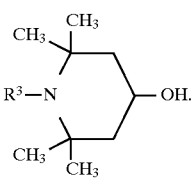

Piperidine compounds of this type are known in general terms and some are commercially available. Either their preparation is known or they can be prepared analogously to known processes.

For the preparation of a compound of the formula V or VI, the corresponding piperidine compound can first be reacted in a manner known per se with epichlorohydrin with elimination of HCl to give the intermediate of the formula Vb

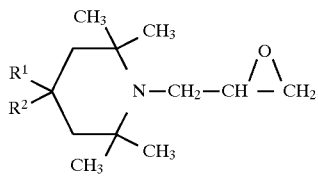

or of the formula VIb respectively

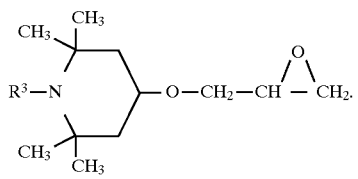

This can subsequently be reacted with an ethylenically unsaturated monobasic or dibasic carboxylic acid or an ethylenically unsaturated monohydric or dihydric phenol of the formula

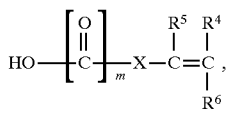

with formation of the compound of the formula V or VI. The symbols m, $R^1$, $R^2$, $R^3$, $R^4$, $R^5$ and $R^6$ are as defined above.

The epoxidized intermediate of the formula Vb or VIb can be prepared correspondingly or analogously to one of the methods described in EP-A-001 835 or in Luston and Vass, Makromol. Chem., Macromol. Symp. 27, 231 (1989). The piperidine compound of the formula Va or VIa is expediently treated slowly with an excess of epichlorohydrin in the presence of strong bases, for example aqueous concentrated alkali metal hydroxide solution, and in the presence of an organic solvent.

The base is advantageously employed in an approximately 2–20-fold molar excess, based on the compound of the formula Va or VIa; for example, 3–15 mol, preferably 4–12 mol, of sodium hydroxide or potassium hydroxide as a 50% aqueous solution are used per mol of piperidine compound. The organic solvent is expediently used in such an amount that the compound of the formula Va or VIa is dissolved completely; examples of suitable solvents are low-polarity to non-polar solvents such as hydrocarbons and ethers; toluene is preferred.

For example, 1–4 equivalents, preferably 1.2–3 equivalents, in particular 1.5–2.5 equivalents, of epichlorohydrin can be employed per equivalent of the piperidine compound of the formula Va or VIa. In addition, 1–30 mol %, preferably 5–25 mol %, of a tertiary amine salt, for example a tetraalkylammonium halide, such as tetramethylammonium chloride or tetrabutylammonium bromide, or of a phosphonium salt, for example a quaternary phosphonium halide, such as ethyltriphenylphosphonium bromide, can advantageously be added to the mixture as catalyst.

The temperature during the reaction is expediently 0–100° C., preferably 20–80° C., in particular 30–70° C.

When the reaction is complete, the work-up can be carried out by conventional methods; the mixture is expediently first diluted with water, for example by transferring the reaction mixture into 1–4 times the volume of ice water, and the organic phase can subsequently be separated off directly or extracted, for example using ethyl acetate. After the organic phase has been dried, the product can be isolated by removing the solvent. It is also possible to use further purification steps, such as dispersion of activated charcoal, filtration and/or distillation.

The further reaction of the intermediate of the formula Vb or VIb with opening of the epoxide to give the compound of the formula V or VI can be carried out with or without solvent; any solvents used are polar or non-polar, inert and preferably high-boiling. Thus, for example, it is equally possible to use aromatic or aliphatic hydrocarbons and heterocyclic solvents, ethers, sulfones, sulfoxides or amides; preferred solvents include relatively high-boiling hydrocarbon fractions, such as ligroin or petroleum ether, aromatic hydrocarbons, such as toluene or xylene, decalin, cyclic or open-chain ethers, such as dibutyl ether or dioxane, dimethylformamide or dimethyl sulfoxide; toluene and xylene are particularly preferred.

The temperature of the reaction mixture can be kept in the boiling range (reflux) for the duration of the reaction. To this end, a solvent-containing reaction mixture is warmed to the boiling point, generally under atmospheric pressure, and the evaporated solvent is condensed with the aid of a suitable condenser and fed back into the reaction mixture. The boiling range of the pure solvent can, where appropriate, be in the range 60–180° C. for example 60–140° C. If a carboxylic acid is employed for the reaction, the temperature is preferably kept in the range 30–130° C., in particular 40–90° C., and the reaction duration is, for example, from 1 to 20 hours. If a phenol is used, the temperature is preferably kept in the range 80–180° C., in particular 100–160° C., and the reaction duration is, for example, from 3 to 36 hours.

The reaction is preferably carried out under a protective gas, for example nitrogen or argon; the reaction mixture is expediently stirred. The epoxide of the formula Vb or VIb is preferably employed in an approximately equivalent amount or in a slight excess relative to the carboxylic acid groups or the phenolic hydroxyl groups of the reactant, for example in an amount of from 1.0 to 1.3 equivalents, in particular from 1.0 to 1.15 equivalents, per equivalent of phenolic OH or carboxylic acid.

The reaction is preferably carried out in the presence of a tertiary amine salt, for example a tetraalkylammonium halide, for example tetramethylammonium chloride or tetrabutylammonium bromide, or of a phosphonium salt, for example a quaternary phosphonium halide, such as ethyltriphenylphosphonium bromide, as catalyst. The catalyst is expediently employed in an amount of from 1 to 5 mol %, based on the compound of the formula Vb or VIb.

The work-up after completion of the reaction can be carried out by customary methods; for example, the cooled mixture is first washed with the aqueous solution of a base, for example very dilute alkali metal hydroxide solution, and subsequently with water, then dried, and the solvent is then removed, for example by applying a reduced pressure and/or by warming. The drying can be followed by further purification steps, such as dispersion of activated charcoal, filtration, distillation, etc.

In a further possible preparation process for the novel compounds of the formula V or VI, epichlorohydrin is first reacted with the carboxylic acid or with the phenol, and the resultant intermediate is subsequently reacted with the piperidine compound of the formula Va or VIa with opening of the epoxide ring to give the desired compound of the formula V or VI.

Compounds of the formula Vb can furthermore be obtained by oxidation of the corresponding N-allyl compounds with the aid of peracids, for example peracetic acid. The remainder of the reaction can be carried out as described above.

Homopolymers or copolymers comprising structural units of the formula I and/or II and compounds of the formula V and of the formula VI are suitable for the stabilization of organic polymers against thermal, oxidative and actinic degradation.

Examples of such materials are:
1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), low density polyethylene (LDPE), linear low density polyethylene (LLDPE), branched low density polyethylene (BLDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either $\pi$- or $\sigma$-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals beeing elements of groups Ia, IIa and/or IIIa of the Periodic Table. The activators may be modified conveniently with further ester, ether, amine or silyl ether groups. These catalyst stystems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

5. Polystyrene, poly(p-methylstyrene), poly($\alpha$-methylstyrene).

6. Copolymers of styrene or $\alpha$-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

7. Graft copolymers of styrene or $\alpha$-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from $\alpha,\beta$-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.
11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.
12. Homopolymers and copolymers of cyclic ethers such as polyalkylene glycols, polyethylene oxide, polypropylene oxide or copolymers thereof with bisglycidyl ethers.
13. Polyacetals such as polyoxymethylene and those polyoxymethylenes which contain ethylene oxide as a comonomer; polyacetals modified with thermoplastic polyurethanes, acrylates or MBS.
14. Polyphenylene oxides and sulfides, and mixtures of polyphenylene oxides with styrene polymers or polyamides.
15. Polyurethanes derived from hydroxyl-terminated polyethers, polyesters or polybutadienes on the one hand and aliphatic or aromatic polyisocyanates on the other, as well as precursors thereof.
16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).
17. Polyureas, polyimides, polyamide-imides and polybenzimidazoles.
18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.
19. Polycarbonates and polyester carbonates.
20. Polysulfones, polyether sulfones and polyether ketones.
21. Crosslinked polymers derived from aldehydes on the one hand and phenols, ureas and melamines on the other hand, such as phenouformaldehyde resins, urea/formaldehyde resins and melamine/formaldehyde resins.
22. Drying and non-drying alkyd resins.
23. Unsaturated polyester resins derived from copolyesters of saturated and unsaturated dicarboxylic acids with polyhydric alcohols and vinyl compounds as crosslinking agents, and also halogen-containing modifications thereof of low flammability.
24. Crosslinkable acrylic resins derived from substituted acrylates, for example epoxy acrylates, urethane acrylates or polyester acrylates.
25. Alkyd resins, polyester resins and acrylate resins crosslinked with melamine resins, urea resins, polyisocyanates or epoxy resins.
26. Crosslinked epoxy resins derived from polyepoxides, for example from bisglycidyl ethers or from cycloaliphatic diepoxides.
27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.
28. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO.

The invention therefore furthermore relates to compositions comprising (a) an organic polymer which is sensitive to damage by light, oxygen and/or heat, and (b), as stabilizer, a polymer comprising structural units of the formula I and/or II, and to the use of the abovementioned polymers or copolymers for the stabilization of organic polymers against damage by light, oxygen and/or heat.

The invention likewise relates to a process for the stabilization of organic polymers against damage by light, oxygen and/or heat, which comprises admixing, as stabilizer, a polymer or copolymer comprising structural units of the formula I and/or II or a compound of the formula V or of the formula VI, or a mixture of such monomeric or polymeric compounds, to the polymers. The invention preferably relates to a process for the stabilization of organic polymers against damage by light, oxygen and/or heat, which comprises admixing, as stabilizer, a polymer or copolymer comprising structural units of the formula I and/or II to the polymers.

Of particular interest is the use of the novel polymers or copolymers as stabilizers in synthetic organic polymers, in particular thermoplastics, for example polyolefins.

The organic polymers to be protected are preferably natural, semisynthetic or preferably synthetic organic polymers. Particular preference is given to synthetic organic polymers or mixtures of such polymers, in particular thermoplastics, such as polyolefins, especially polyethylene and polypropylene (PP). Other particularly preferred organic materials are coating compositions. The term photographic materials is taken to mean, in particular, the materials described in Research Disclosure 1990, 31429 (pages 474–480) for photographic reproduction and other reproduction methods. Coating compositions advantageously to be stabilized in the context of the invention are described, for example, in Ullmann's Encyclopedia of Industrial Chemistry, 5th Edn., Vol. A18, pp. 359–464, VCH Verlagsgesellschaft, Weinheim 1991.

The invention therefore particularly preferably relates to compositions in which the component (a) to be protected is a polyolefin or a surface-coating binder based on acrylic, alkyd, polyurethane, polyester or polyamide resin or corresponding modified resins.

In general, the novel polymers or copolymers or the novel monomers of the formula V or VI are added to the material to be stabilized in amounts of from 0.01 to 10%, preferably from 0.01 to 5%, in particular from 0.01 to 2%, based on the total weight of the stabilized composition. The compounds according to the invention are particularly preferably employed in amounts of from 0.05 to 1.5%, in particular from 0.1 to 1.5%.

The incorporation into the materials to be stabilized can be carried out, for example, by mixing or application of the novel polymers or copolymers and any further additives by conventional methods. For example, the incorporation into the polymers to be protected can be carried out before or during moulding, or by application of the dissolved or dispersed compound to the polymer, if necessary with subsequent evaporation of the solvent. In the case of elastomers, these can also be stabilized as lattices. Another method of incorporating the novel polymers or copolymers comprises adding them before, during or directly after polymerization of the corresponding monomers or before the crosslinking. The novel polymers or copolymers can be added as such or in encapsulated form (for example in waxes, oils or further polymers). In the case of addition before or during the polymerization, the novel polymers or copolymers can also act as regulators for the chain length of the polymers (chain terminators).

The novel polymers or copolymers can also be added to the plastics to be stabilized in the form of a masterbatch which contains this compound, for example, in a concentration of from 2.5 to 25% by weight.

A particular form of such masterbatches comprises graft copolymers comprising from 2 to 20 mol % of structural units of the formula I and/or II. Preference is given to graft copolymers whose backbone is formed from a polyolefin, for example polyethylene or polypropylene, and whose side chains are formed from structural units of the formula I and/or II.

The incorporation of the novel polymers or copolymers can expediently be carried out by the following methods:
- as an emulsion or dispersion (for example to lattices or emulsion polymers),
- as a dry mix during the mixing of additional components or polymer mixtures,
- by direct addition into the processing apparatus (for example extruder, internal mixer etc.),
- as a solution or melt.

The polymer compositions according to the invention can be used in various forms or converted into various products, for example they can be used as or converted into films, fibres, tapes, moulding compositions, profiles or as binders for surface coatings, adhesives or adhesive cements.

In addition to the novel polymers or copolymers, the compositions according to the invention can additionally contain conventional additives, for example those mentioned below.

The conventional additives are expediently employed in amounts of 0.1–10% by weight, for example 0.2–5% by weight, based on the polymer to be stabilized.

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, 2,6-di-nonyl-4-methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1'-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis-(3,5-di-tert-butyl-4-hydroxyphenyl)adipate.

1.4. Tocopherols, for example α-tocopherol, β-tocopherol, γ-tocopherol, δ-tocopherol and mixtures thereof (Vitamin E).

1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis-(3,6-di-sec-amylphenol), 4,4'-bis-(2,6-dimethyl-4-hydroxyphenyl)disulfide.

1.6. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl)butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis-(3,5-di-tert-butyl-4-hydroxyphenyl)propane, 2,2-bis-(5-tert-butyl-4-hydroxy2-methylphenyl)-4-n-dodecylmercaptobutane, 1,1,5,5-tetra-(5-tert-butyl-4-hydroxy2-methylphenyl) pentane.

1.7. O-, N- and S-benzyl compounds, for example 3,5,3',5'-tetra-tert-butyl-4,4'-dihydroxydibenzyl ether, octadecyl-4-hydroxy-3,5-dimethylbenzylmercaptoacetate, tris-(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5di-tert-butyl-4-hydroxybenzylmercaptoacetate.

1.8. Hydroxybenzylated malonates, for example dioctadecyl-2,2-bis-(3,5-di-tert-butyl-2-hydroxybenzyl)-malonate, di-octadecyl-2-(3-tert-butyl-4-hydroxy-5-methylbenzyl)-malonate, di-dodecylmercaptoethyl-2,2-bis-(3,5-di-tert-butyl-4-hydroxybenzyl)malonate, bis-[4-(1,1,3,3-tetramethylbutyl)phenyl]-2,2-bis(3,5-di-tert-butyl-4-hydroxybenzyl)malonate.

1.9. Aromatic hydroxybenzyl compounds, for example 1,3,5-tris-(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris (3,5-di-tert-butyl-4-hydroxybenzyl)phenol.

1.10. Triazine Compounds, for example 2,4-bis (octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris-(3,5-di-tert-butyl-4-hydroxybenzyl)isocyanurate, 1,3,5-tris(4-tert-butyl-3-hydroxy-2,6-dimethylbenzyl)isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-di-tert-butyl-4-hydroxyphenyl) propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis (hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters β-(5-tert-butyl-4-hydroxy-3-methylphenyl) propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis (hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15. Esters of β-(3,5-dicyclohexyl-4-hydroxyphenyl) propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis (hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis (hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-4-hydroxyphenyl) propionic acid e.g. N,N'-bis(3,5-di-tert-butyl-4-hydroxyphenylpropionyl)hexamethylenediamine, N,N'-bis(3,5-di-tert-butyl-4-hydroxyphenylpropionyl)trimethylenediamine, N,N'-bis(3,5-di-tert-butyl-4-hydroxyphenylpropionyl)hydrazine.

2. UV absorbers and light stabilisers 2.1. 2-(2'-Hydroxyphenyl)benzotriazoles, for example 2-(2'-hydroxy-5'-methylphenyl)benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl) benzotriazole, 2-(3',5'-di-tert-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl)benzotriazole, 2-(2'-hydroxy-4'-octyloxyphenyl)benzotriazole, 2-(3',5'-di-tert-amyl-2'-hydroxyphenyl)benzotriazole, 2-(3',5'-bis-(α,α-dimethylbenzyl)-2'-hydroxyphenyl) benzotriazole, mixture of 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)-carbonylethyl]- 2'-hydroxyphenyl)-5-chloro-benzotriazole, 2-(3'-tert-butyl-2'-hydroxy-5'-(2-methoxycarbonylethyl)phenyl)-5-chloro-benzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl) phenyl)benzotriazole, 2-(3'-tert-butyl-5'-[2-(2-ethylhexyloxy)carbonylethyl]-2'-hydroxyphenyl) benzotriazole, 2-(3'-dodecyl-2'-hydroxy-5'-methylphenyl)benzotriazole, and 2-(3'-tert-butyl-2'-hydroxy-5'-(2-isooctyloxycarbonylethyl) phenylbenzotriazole, 2,2'-methylene-bis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300; [R—CH$_2$CH$_2$—COO(CH$_2$)$_3$]$_2$, where R=3'-tert-butyl-4'-hydroxy-5'-2H-benzotriazol-2-ylphenyl.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, as for example 4-tertbutylphenyl salicylate, phenyl salicylate, octylphenyl salicylate, dibenzoyl resorcinol, bis(4-tetert-butylbenzoyl)resorcinol, benzoyl resorcinol, 2,4-di-tertbutylphenyl 3,4-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxy-cinnamate, butyl α-cyano-β-methyl-p-methoxy-cinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis-[4-(1,1,3,3-tetra-methylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, with or without additional ligands.

2.6. Sterically hindered amines, for example bis(2,2,6,6-tetramethyl-piperidyl)sebacate, bis(2,2,6,6-tetramethyl-piperidyl)succinate, bis(1,2,2,6,6-pentamethylpiperidyl)sebacate, bis(1,2,2,6,6-pentamethylpiperidyl)n-butyl-3,5-di-tert-butyl-4-hydroxybenzylmalonate, the condensate of 1-(2-hydroxyethyl)-2,2,6,6-tetramethyl-4-hydroxypiperidine and succinic acid, the condensate of N,N'-bis(2,2,6,6-tetramethyl-4-piperidyl)hexamethylenediamine and 4-tert-octylamino-2,6-dichloro-1,3,5-triazine, tris(2,2,6,6-tetramethyl-4-piperidyl)nitrilotriacetate, tetrakis(2,2,6,6-tetramethyl-4-piperidyl)-1,2,3,4-butane-tetracarboxylate, 1,1'-(1,2-ethanediyl)bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazasprio[4.5]decan-2,4-dion, bis(1-octyloxy-2,2,6,6-tetramethylpiperidyl)sebacate, bis(1-octyloxy-2,2,6,6-tetramethylpiperidyl)succinate, the condensate of N,N'-bis-(2,2,6,6-tetramethyl-4-piperidyl)hexamethylenediamine and 4-morpholino-2,6-dichloro-1,3,5-triazine, the condensate of 2-chloro-4,6-bis(4-n-butyl-amino-2,2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidin-2,5-dione, 3-dodecyl-1-(1,2,2,6,6-pentamethyl-4-piperidyl)pyrrolidine-2,5-dione.

2.7. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide and mixtures of ortho- and para-methoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-[2-hydroxy-4-(2hydroxy-3-butyloxy-propoxy)phenyl]-4,6-bis(2,4-dimethyl)-1,3,5-triazine, 2-[2-hydroxy-4-(2-hydroxy-3-octyloxy-propyloxy)phenyl]-4,6-bis(2,4-dimethyl)-1,3,5-triazine.

3. Metal deactivators, for example N,N'-diphenyloxamide, N-salicylal-N'-salicyloyl hydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl) oxalyl dihydrazide, N,N'-bis(salicyloyl)thiopropionyl dihydrazide.

4. Phosphites and phosphonites, for example triphenyl phosphite, diphenyl alkyl phosphites, phenyl dialkyl phosphites, tris(nonylphenyl)phosphite, trilauryl phosphite, trioctadecyl phosphite, distearyl pentaerythritol diphosphite, tris(2,4-di-tert-butylphenyl)phosphite, diisodecyl pentaerythritol diphosphite, bis(2,4-di-tert-butylphenyl) pentaerythritol diphosphite, bis(2,6-di-tert-butyl-4-methylphenyl)-pentaerythritol diphosphite, diisodecyloxypentaerythritol diphosphite, bis(2,4-di-tert-butyl-6-methylphenyl)pentaerythritol diphosphite, bis(2,4,6-tris(tert-butylphenyl)pentaerythritol diphsophite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenz[d,g]-1,3,2-dioxaphosphocin, 6-fluoro-2,4,8,10-tetra-tert-butyl-12-methyl-dibenz[d,g]-1,3,2-dioxaphosphocin, bis(2,4-di-tert-butyl-6-methylphenyl) methylphosphite, bis(2,4-di-tert-butyl-6-methylphenyl) ethylphosphite.

5. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

6. Polyamide stabilisers, for example, copper salts in combination with iodides and/or phosphorus compounds and salts of divalent manganese.

7. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example calcium stearate, zinc stearate, magnesium behenate, magnesium stearate, sodium ricinoleate and potassium palmitate, antimony pyrocatecholate or tin pyrocatecholate.

8. Nucleating agents, for example, 4-tert-butylbenzoic acid, adipic acid, diphenylacetic acid.

9. Fillers and reinforcing agents, for example, calcium carbonate, silicates, glass fibres, asbestos, talc, kaolin, mica, barium sulfate, metal oxides and hydroxides, carbon black, graphite.

10. Other additives, for example, plasticisers, lubricants, emulsifiers, pigments, optical brighteners, flameproofing agents, antistatic agents and blowing agents.

11. Benzofuranones and indolinones, for example those disclosed U.S. Pat. No. 4,325,863, U.S. Pat. No. 4,338,244, U.S. Pat. No. 5,175,312, U.S. Pat. No. 5,216,052, U.S. Pat. No. 5,252,643, DE-A-4 316 611, DE-A-4 316 622, DE-A-4 316 876, EP-A-0 589 839 or EP-A-0 591 102 or 3-[4-(2-acetoxyethoxy)phenyl]-5,7-di-tert-butyl-benzofuran-2-one, 5,7-di-tert-butyl-3-[4-(2-stearoyloxyethoxy)phenyl]benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butyl-benzofuran-2-one, 3-(3, 5-dimethyl-4-pivaloyloxyphenyl)-5,7-di-tert-butyl-benzofuran-2-one.

The examples below illustrate the invention in greater detail. All parts and percentages, whether in the examples, in the remainder of the description or in the claims, are by weight, unless specified otherwise. The following abbreviations are used in the examples:
DMF: dimethylformamide
THF: tetrahydrofuran
GC: gas chromatography
HPLC: high-pressure liquid chromatography
GPC: gel permeation chromatography
DSC: differential scanning calorimetry
TGA: thermogravimetric analysis
AIBN: α,α'-azoisobutyronitrile
$M_n$: number average molecular weight (unit g/mol)
$M_w$: weight average molecular weight (unit g/mol).

Preparation Examples

A) Preparation of the monomers

A1) 4-(3-Acryloxy-2-hydroxypropoxy)-1,2,2,6,6-pentamethylpiperidine

A1a) 1,2,2,6,6-Pentamethyl-4-(2,3-epoxypropoxy)piperidine 300 g (7.5 mol) of sodium hydroxide are dissolved in 300 g of water under an argon atmosphere in a 2.5 l sulfonation flask fitted with mechanical stirrer, condenser and 500 ml dropping funnel. 750 ml of toluene, 48.4 g (0.15 mol) of tetrabutylammonium bromide and 257 g (1.5 mol) of 4-hydroxy-1,2,2,6,6-pentamethylpiperidine are added. 347 g (3.75 mol) of epichlorohydrin are added dropwise at 60° C. over the course of 1.5 hours, and the mixture is subsequently stirred at the same temperature for a further 4 hours. The reaction solution is poured into 3 l of ice water, and the organic phase is separated off, dried using sodium sulfate and evaporated. The residue is distilled at 0.05 mmHg over a Vigreux column, and the fraction of boiling point 71–72° C. is collected.

Yield: 205 g (60%). GC: >99%

| | Microanalysis | |
|---|---|---|
| | calculated | found |
| C | 68.68 | 68.64 |
| H | 11.07 | 11.21 |
| N | 6.16 | 6.32 |
| Cl | 0.0 | 0.0 |

$^1$H-NMR (CDCl$_3$): 1.02 and 1.16 ppm (12H, s): CH$_3$ groups of the piperidine ring 1.32–1.4 ppm and 1.83–1.91 ppm (4H, m): CH$_2$ groups of the piperidine ring 2.23 ppm (3H, s): N—CH$_3$ 2.60–2.62 ppm and 2.78–2.82 ppm (2H, m): CH$_2$ group of the epoxide ring 3.42–3.47 ppm and 3.71–3.76 ppm (2H, m): O—CH$_2$ group 3.57–3.67 ppm (1H, m): CH—O of the piperidine ring A1b) 4-(3-Acryloxy-2-hydroxypropoxy)-1,2,2,6,6-pentamethylpineridine 375 g (1.65 mol) of 4-(2,3-epoxypropoxy)-1,2,2,6,6-pentamethylpiperidine (=A1a) in 1.5l of xylene are introduced under argon into a 2.5 l sulfonation flask fitted with magnetic stirrer, thermometer and condenser. 108 g (1.5 mol) of acrylic acid and 27.8 g (75 mmol) of ethyltriphenylphosphonium bromide are added. The reactants are allowed to react at 70° C. for 18 hours. The cooled product is poured into ice water, and the organic phase is separated off, washed twice with 1N sodium hydroxide solution, dried and evaporated. The residue is distilled over a short Vigreux column. 193 g (43%) of the title product are obtained as a clear liquid of boiling point 119–125° C. (0.06 mmHg).

| | Microanalysis | |
|---|---|---|
| | calculated | found |
| C | 64.18 | 63.50 |
| H | 9.76 | 9.76 |
| N | 4.68 | 4.67 |

$^1$H-NMR (CDCl$_3$): 1.02 and 1.16 ppm (12H,s): CH$_3$ (piperidine) 1.33–1.40 and 1.84–1.89 ppm (4H, m): CH$_2$ (piperidine) 2.23 ppm (3H, s): N—CH$_3$ 2.59 ppm (1H, s): OH 3.46–3.63 and 3.71–3.72 and 3.84–3.86 and 3.98–4.05 and 4.18–4.29 ppm (6H, m):

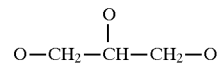

and CH (piperidine) 5.84–5.88 and 6.12–6.22 and 6.42–6.48 ppm (3H, m): CO—CH=CH$_2$ A2) 4-(3-Methacryloxy-2-hydroxypropoxy)-1,2,2,6,6-pentamethylpiperidine 250 g (1.1 mol) of 4-(2,3-epoxypropoxy)-1,2,2,6,6-pentamethylpiperidine are dissolved in 1 l of xylene under a protective gas in a 1.5 l sulfonation flask fitted with magnetic stirrer, thermometer and condenser. 86 g (1 mol) of methacrylic acid and 18.6 g (50 mmol) of ethyltriphenylphosphonium bromide are added. The mixture is stirred at 70° C. for 18 hours, cooled and poured into ice water, and the organic phase is separated off, washed twice with 1N sodium hydroxide solution and dried. The solvent is evaporated off in a Rotavap, and the residue is distilled at 0.07 mmHg, giving 176.5 g (56%) of a clear liquid which boils at 128–130° C.

| | Microanalysis | |
|---|---|---|
| | calculated | found |
| C | 64.14 | 64.72 |
| H | 9.97 | 10.00 |
| N | 4.47 | 4.33 |

$^1$H-NMR (CDCl$_3$): 1.01 and 1.16 ppm (12H,s): CH$_3$ (piperidine) 1.32–1.40 and 1.83–1.88 ppm (4H, m): CH$_2$ (piperidine) 1.96 ppm (3H, s): CH$_3$ (methacrylate) 2.23 ppm (3H, s): CH$_3$—N 2.68 ppm (1H, s): OH 3.46–4.26 ppm (6H, m):

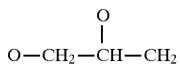

and CH (piperidine) 5.59 and 6.14 ppm (2H, s): CH$_2$=C

A3) 4-(3-[4-Vinylbenzoxy]-2-hydroxypropoxy)-1,2,2,6,6-pentamethylpiperidine 32.6 g (220 mmol) of 4-vinylbenzoic acid, 45.5 g (200 mmol) of 4-(2,3-epoxypropoxy)-1,2,2,6,6-pentamethylpiperidine, 3.7 g (10 mmol) of ethyltriphenylphosphonium bromide and 200 ml of xylene are introduced into a 500 ml round-bottom flask fitted with magnetic stirrer, condenser, thermometer and argon balloon. The mixture is warmed to 65° C. under a protective gas. The clear solution is held at 65° C. for 15 hours and then poured onto ice. The organic phase is washed twice at 0° C. with 1N sodium hydroxide solution, dried over sodium sulfate and evaporated. The residue is purified over a silica-gel column (THF) and dried at 60° C. in a high vacuum, giving 52.7 g (70%) of a clear, viscous liquid.

| Microanalysis | calculated | found |
|---|---|---|
| C | 70.37 | 69.89 |
| H | 8.86 | 9.22 |
| N | 3.73 | 3.79 |

$^1$H-NMR (CDCl$_3$): 1.01 and 1.15 ppm (12H, s): CH$_3$ 1.33–1.43 and 1.84–1.89 ppm (4H, m): CH$_2$ (piperidine) 2.23 ppm (3H, s): N—CH$_3$ 2.81 ppm (1H, s): OH 3.42–4.40 ppm (6H, m):

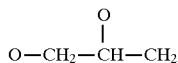

and CH (piperidine) 5.36–5.40 ppm and 5.83–5.89 ppm (2H, d): CH$_2$= 6.70–6.79 ppm (1H, q): CH= 7.44–7.47 ppm and 7.99–8.02 ppm (4H, d): aromatic A4) 1-(3-[4-Vinylbenzoxy]-2-hydroxypropyl)-4-benzyloxyl-2,2,6,6-tetramethylpiperidine 53 g (175 mmol) of 1-(2,3-epoxypropyl)-4-benzoxy-2,2,6,6-tetramethylpiperidine, 28.5 g (192 mmol) of 4-vinylbenzoic acid, 3,2 g (8.7 mmol) of ethyltriphenylphosphonium bromide and 200 ml xylene are introduced into a 500 ml round-bottom flask fitted with magnetic stirrer, thermometer, condenser and argon balloon. The mixture is stirred at 65° C. for 15 hours and then poured onto ice. Work-up as in the above examples and column chromatography (silica gel; hexane/ethyl acetate=3:1) give a colourless, viscous liquid.

Yield: 55.1 g (70%)

| Microanalysis | calculated | found |
|---|---|---|
| C | 74.47 | 74.11 |
| H | 8.26 | 8.26 |
| N | 3.10 | 3.08 |

$^1$H-NMR (CDCl$_3$): 0.99–1.21 ppm (12H, s): CH$_3$ 1.50 ppm and 1.96 ppm (4H, m): CH$_2$ (piperidine) 2.52–2.60 ppm and 2.72–2.86 ppm (2H, m): N—CH$_3$ 3.72–3.81 ppm (2H, m): =CH—OH 4.17–4.23 ppm (1H, m): CH (piperidine) 4.35–4.40 ppm (2H, s): CH$_2$—O-aromatic 5.35–5.39 ppm and 5.83–5.88 ppm (2H, d): CH$_2$= 6.69–6.79 ppm (1H, q): CH= 7.25–7.35 ppm (5H, m): benzyl aromatic 7.43–7.46 and 8.01–8.04 ppm (4H, d): benzoic acid aromatic A5) 1-(3-Acryloxy-2-hydroxypropyl)-4-benzyloxyl-2,2,6,6-tetramethylpiperidine 50 g (165 mmol) of 1-(2,3-Epoxypropyl)-4-benzoxy-2,2,6,6-tetramethylpiperidine, 13.1 g (181 mmol) of acrylic acid and 3.06 g (8.3 mmol) of ethyltriphenylphosphonium bromide are reacted in 200 ml of xylene analogously to A4). The reaction product is washed with sodium hydroxide solution at 0° C. and worked up, giving 39 g (63%) of a clear, viscous liquid.

| Microanalysis: | % C | % H | % N |
|---|---|---|---|
| calculated | 70.37 | 8.86 | 3.73 |
| found | 70.40 | 8.97 | 3.49 |

$^1$H-NMR (CDCl$_3$): 1.00–1.29 ppm (12H,m): CH$_3$ 1.49 and 1.97 ppm (4H, m): CH$_2$ (piperidine) 2.46–2.54 ppm and 2.67–276 ppm (2H, m): N—CH$_2$ 3.70–3.79 ppm (2H, m):

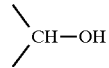

4.00–4.06 ppm (1H, m): CH (piperidine) 4.22–4.46 ppm (2H, m): COO—CH$_2$— 4.56 ppm (2H, s): O—CH$_2$-aromatic 5.82–5.85 ppm and 6.12–6.21 ppm and 6.42–6.48 ppm (3H, m): acrylyl group 7.26–7.35 ppm (5H, m): aromatic A6) 1-(3-Methacryloxy-2-hydroxyproplyl)-4-benzyloxyl-2,2,6,6,-tetramehtylpiperidine The preparation is carried out analogously to A5) giving 54 g (84%) of a clear, viscous liquid.

| Microanalysis: | % C | % H | % N |
|---|---|---|---|
| calculated | 70.92 | 9.06 | 3.60 |
| found | 70.89 | 9.08 | 3.47 |

$^1$H-NMR (CDCl$_3$): 1.00–1.21 ppm (12H, m): CH$_3$ (piperidine) 1.48 ppm (2H, m): CH$_2$ (piperidine) 1.94–1.96 ppm (5H, m): CH$_2$ (piperidine), CH$_3$ (methacrylate) 2.47–2.55 and 2.67–2.74 ppm (2H, m): N—CH$_2$— 3.71–3.79 ppm (2H, m):

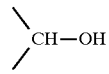

4.00–4.06 ppm (1H, m): CH (piperidine) 4.18–4.28 ppm (2H, m): —COO—CH$_2$— 4.55 ppm (2H, s): O—CH$_2$-aromatic 5.58 ppm and 6.15 ppm (2H, s): CH$_2$=C 7.26–7.34 ppm (5H, m): aromatic A7) 1-(3-[4-Vinylphenoxy]-2-hydroxypropyl)-4-benzyloxyl-2,2,6,6-tetramethylpiperidine 43.3 g (360 mmol) of 4-hydroxystyrene, 91 g (300 mmol) of 1-(2,3-epoxypropyl)-4-benzoxy-2,2,6,6-tetramethylpiperidine, 5.6 g (15 mmol) of ethyltriphenylphosphonium bromide, 1.3 g (6 mmol) of di-tert-butylcresol and 250 ml of dioxane are introduced into a 500 ml sulfonation flask fitted with magnetic stirrrer, condenser and argon balloon. The reaction mixture is kept at the reflux temperature for 14 hours with stirring and subsequently poured into ice/ethyl acetate, and the organic phase is washed twice at 0° C. with 1N NaOH, dried and evaporated. The solid is recrystallized from n-hexane, giving 100 g (78%) of a colourless substance which melts at 86° C.

| Microanalysis: | % C | % H | % N |
|---|---|---|---|
| calculated | 76.56 | 8.80 | 3.31 |
| found | 76.49 | 8.84 | 3.19 |

$^1$H-NMR (CDCl$_3$): 0.96–1.18 ppm (12H, m): CH$_3$ 1.38–1.50 and 1.95–2.02 ppm (4H, m): CH$_2$ (piperidine)

2.62–2.85 ppm (2H, m): N—CH$_2$— 3.73–4.02 ppm (3H, m): O—CH$_2$—CH 4.35 ppm (1H, s): OH 4.57 ppm (2H, s): O—CH$_2$Ar 5.10–5.14 ppm and 5.57–5.63 ppm (2H, d): CH$_2$= 6.61–6.70 ppm (1H, q): CH= 6.87–6.90 ppm and 7.25–7.35 ppm (9H, d, m): H-aromatic A8) 4-(3-[4-Vinylphenoxy]-2-hydroxypropoxy)-1,2,2,6,6-pentamethylpiperidine 28.8 g (240 mmol) of 4-vinylphenol are reacted with 45.5 g (200 mmol) of 4-(2,3-epoxypropoxy)-1,2,2,6,6-pentamethylpiperidine analogously to Example A7).

Yield: 66 g (95%)

| Microanalysis: | % C | % H | % N |
|---|---|---|---|
| calculated | 72.58 | 9.57 | 4.03 |
| found | 72.67 | 9.53 | 3.89 |

$^1$H-NMR (CDCl$_3$): 1.01 and 1.15 ppm (12H, s): CH$_3$ (piperidine) 1.32–1.41 ppm and 1.84–1.89 ppm (4H, m): CH$_2$ (piperidine) 2.23 ppm (3H, s): N—CH$_3$ 2.72 ppm (1H, s): OH 3.54–3.69 ppm (3H, m): Pip-O—CH$_2$—CH— 3.98–4.03 ppm (2H, d): ar-O—CH$_2$— 4.06–4.12 ppm (1H, m):

5.11–5.14 ppm and 5.58–5.64 ppm (2H, d): CH$_2$= 6.60–6.70 ppm (1H, q): CH= 6.86–6.89 ppm and 7.32–7.35 ppm (4H, d): H-aromatic

EXAMPLES A9–A14

The monomers shown in the table below are prepared by the method described under A1 by reacting the corresponding epoxide with the corresponding acid:

| Example | Monomer | Epoxide | Acid |
|---|---|---|---|
| A9 | 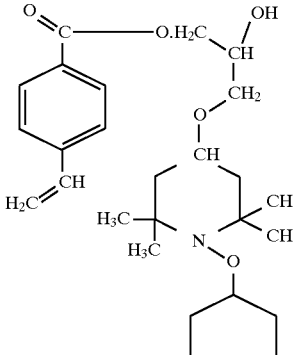 | 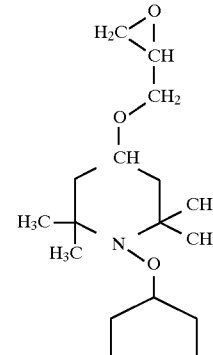 | 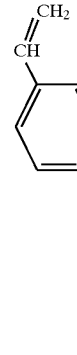 |
| A10 | 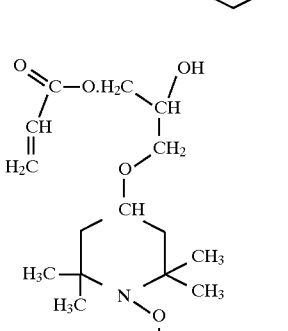 | 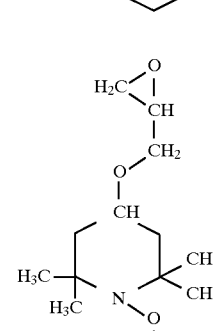 | 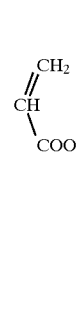 |

-continued

| Example | Monomer | Epoxide | Acid |
|---------|---------|---------|------|
| A11 | (structure) | (structure) | (structure) |
| A12 | (structure) | (structure) | (structure) |
| A13 | (structure) | (structure) | (structure) |
| A14 | (structure) | (structure) | (structure) |

A15) 4-(3-[4-Vinylphenoxy]-2-hydroxypropoxy)-1-cyclohexyloxy-2,2,6,6-tetramethylpiperidine 4-Vinylphenol is reacted with 4-(2,3-epoxypropoxy)-1-cyclohexyloxy-2,2,6,6-tetramethylpiperidine analogously to Example A8), giving the title product.

A16) 4-(3-[4-Vinylphenoxy]-2-hydroxypropoxy)-1-octyloxy-2,2,6,6-tetramethylpiperidine 4-Vinylphenol is reacted with 4-(2,3-epoxypropoxy)-1-octyloxy-2,2,6,6-tetramethylpiperidine analogously to Example A8), giving the title product.

B) Preparation of the polymers

B1) Poly[4-(3-acryloxy)-2-hydroxypropyl)-1,2,2,6,6-pentamethylpiperidine]

60 g (0.2 mol) of the monomer A1), 657 mg (4 mmol) of AIBN and 300 ml of toluene are introduced into a 500 ml round-bottom flask provided with a magnetic stirrer and an argon balloon. The mixture is freed from oxygen by means of vacuum/argon. The mixture is polymerized for 15 hours at 70° C. under argon. The viscous solution is introduced into n-hexane, and semisolid material precipitates, which is redissolved in toluene and precipitated in n-hexane. Drying in a high vacuum gives 35.7 g (60%) of polymer.

| Microanalysis | calculated | found |
|---|---|---|
| C | 64.18 | 64.17 |
| H | 9.76 | 9.88 |
| N | 4.68 | 4.24 |

TGA (N$_2$, 10° C./min): 5% weight loss at 320°
$^1$H-NMR (CDCl$_3$): exhibits no acrylate double bonds
GPC (DMF, 85° C.): M$_n$: 50,000 M$_w$: 165,000

B1a) A further polymerization is carried out as described under B1 with the difference that 0.37 mol of the monomer A1, 3.7 mmol AIBN and, as additional chain transfer catalyst, 74 mmol of butyl mercaptane are used. A polymer is obtained as under B1 having a molecular weight (GPC; DMF, 85° C.) M$_n$=6,800 and M$_w$=8,100.

B1b) A further polymerization is carried out as described under B1 with the difference that for 60 g (0.2 mol) of the monomer A1, 328 mg (2 mmol) AIBN and, as additional chain transfer catalyst, 20 mmol of butyl mercaptane are used. A polymer is obtained as under B1 having a molecular weight (GPC; DMF, 85° C.) M$_n$=12,000 and M$_w$=15,000.

B1c) A further polymerization is carried out as described under B1 with the difference that for 60 g (0.2 mol) of the monomer A1, 328 mg (2 mmol) AIBN and, as additional chain transfer catalyst, 4 mmol of butyl mercaptane are used. A polymer is obtained as under B1 having a molecular weight (GPC; DMF, 85° C.) M$_n$=25,000 and M$_w$=44,000.

B2) Poly[4-(3-methacryloxy]-2-hydroxypropyl)-1,2,2,6,6-pentamethylpiperidine]

EXAMPLE B2a 60 g (0.2 mol) of A2) are polymerized with 624 mg of AIBN in 300 ml of toluene as described under B1), but the re-precipitation is carried out by dissolution in THF and re-precipitation in n-hexane. 53.2 g (89%) of a fine polymer powder are obtained.

| Microanalysis: | calculated | found |
|---|---|---|
| C | 65.14 | 64.72 |
| H | 9.97 | 9.91 |
| N | 4.47 | 4.17 |

$^1$H-NMR (CDCl$_3$): no double bonds visible
TGA (N$_2$, 10° C./min): 5% weight loss at 320°
GPC (DMF, 85° C.): M$_n$: 54,000 M$_w$: 158,000

EXAMPLE B2b

The above procedure (B2a) is repeated and the re-precipitation is carried out as described under Example B1 by dissolving in toluene and re-precipitation in n-hexane, giving a polymer having a molecular weight (GPC; DMF, 85° C.) of M$_n$=93,000 and M$_w$=470,000.

B2c) A further polymerization is carried out as described under B2a with the difference that for 60 g (0.2 mol) of the monomer A2, 328 mg (2 mmol) AIBN and, as additional chain transfer catalyst, 40 mmol of butyl mercaptane are used. A polymer is obtained as under B2a having a molecular weight (GPC; DMF, 85° C.) M$_n$=7,800 and M$_w$=9,200.

B2d) A further polymerization is carried out as described under B2a with the difference that for 60 g (0.2 mol) of the monomer A2, 328 mg (2 mmol) AIBN and, as additional chain transfer catalyst, 20 mmol of butyl mercaptane are used. A polymer is obtained as under B2a having a molecular weight (GPC; DMF, 85° C.) M$_n$=12,000 and M$_w$=15,000.

B2e) A further polymerization is carried out as described under B2a with the difference that for 60 g (0.2 mol) of the monomer A2, 1.6 g (10 mmol) AIBN and, as additional chain transfer catalyst, 10 mmol of butyl mercaptane are used. A polymer is obtained as under B2a having a molecular weight (GPC; DMF, 85° C.) M$_n$=15,000 and M$_w$=21,000.

B2f) A further polymerization is carried out as described under B2a with the difference that for 60 g (0.2 mol) of the monomer A2, 328 mg (2 mmol) AIBN and, as additional chain transfer catalyst, 10 mmol of butyl mercaptane are used. A polymer is obtained as under B2a having a molecular weight (GPC; DMF, 85° C.) M$_n$=17,000 and M$_w$=24,000.

B2g) A further polymerization is carried out as described under B2a with the difference that for 60 g (0.2 mol) of the monomer A2, 328 mg (2 mmol) AIBN and, as additional chain transfer catalyst, 4 mmol of butyl mercaptane are used. A polymer is obtained as under B2a having a molecular weight (GPC; DMF, 85° C.) M$_n$=25,000 and M$_w$=42,000.

B3) Poly{4-[3-(4-vinylbenzoxy)-2-hydroxypropoxy]-1,2,2,6,6-pentamethylpiperidine}

40 g (107 mmol) of A3) are polymerized with 525 mg of AIBN in 120 g of toluene as described under B1), giving 28.8 g (72%) of a white polymer.

| Microanalysis: | calculated | found |
|---|---|---|
| C | 70.37 | 69.79 |
| H | 8.86 | 8.74 |
| N | 3.73 | 3.47 |

$^1$H-NMR (CDCl$_3$): no double bonds visible
TGA (N$_2$, 10° C./min): 10% weight loss at 360° C.
GPC (DMF): M$_n$: 53,000 M$_w$: 123,000

B3a) A further polymerization is carried out as described under B3 with the difference that on 40 g (107 mmol) of the monomer A3, 526 mg (ca. 3 mmol) AIBN and, as additional chain transfer catalyst, 5 mmol of butyl mercaptane are used. A polymer is obtained as under B3 having a molecular weight (GPC; DMF, 85° C.) M$_n$=14,000 and M$_w$=17,000.

B3b) A further polymerization is carried out as described under B3 with the difference that on 40 g (107 mmol) of the monomer A3, 526 mg (ca. 3 mmol) AIBN and, as additional chain transfer catalyst, 10 mmol of butyl mercaptane are used. A polymer is obtained as under B3 having a molecular weight (GPC; DMF, 85° C.) M$_n$=11,000 and M$_w$=12,000.

This polymerization is repeated using 1.05 g (ca. 6 mmol) AIBN; the molecular weight of the polymer (GPC; DMF, 85° C.) is M$_n$=11,000 and M$_w$=12,000.

B4) Poly{1-[3-(vinylbenzoxy)-2-hydroxypropyl]-4-benzoxy-2,2,6,6-tetramethylpiperidine}

51 g (113 mmol) of A4) are polymerized at 70° C. with 557 mg (3.4 mmol) of AIBN in 153 ml toluene as described under B1). Double re-precipitation gives 45.6 g (89%) of a white polymer powder.

| Microanalysis | | |
|---|---|---|
| | calculated | found |
| C | 74.47 | 74.01 |
| H | 8.26 | 8.22 |
| N | 3.10 | 3.00 |

TGA ($N_2$, 10° C./min): 10% weight loss at 320°
GPC (DMF): $M_n$: 52,000 $M_w$: 114,000

B5) Poly[1-(3-acryloxy-2-hydroxypropyl)-4-benzoxy-2,2,6,6-tetramethylpiperidine]

37 g (98.5 mmol) of the compound prepared as described under Example A5) are polymerized at 70° C. with 485 mg of AIBN (3 mmol) in 111 ml of toluene analogously to B1). Double re-precipitation in THF/n-hexane gives 30.1 g (81%) of a white polymer powder.

| Microanalysis: | % C | % H | % N |
|---|---|---|---|
| calculated | 70.37 | 8.86 | 3.73 |
| found | 69.81 | 9.02 | 3.72 |

TGA ($N_2$, 10° C./min): 10% weight loss at 310° C.
DSC ($N_2$, 10° C./min): melting point at 337° C.
GPC (THF): $M_n$: 31,000 $M_w$: 63,000

B6) Poly[1-(3-methacryloxy-2-hydroxypropyl)-4-benzoxy-2,2,6,6-tetramethylpiperidine]

50 g (128 mmol) of the compound prepared as described under Example A6) are polymerized at 70° C. with 632 mg (3.9 mmol) of AIBN in 150 ml of toluene analogously to B1).

Yield: 41.4 g (82%) of a white polymer powder

| Microanalysis: | C % | H % | N % |
|---|---|---|---|
| calculated | 70.92 | 9.06 | 3.60 |
| found | 70.38 | 8.95 | 3.61 |

TGA ($N_2$, 10° C./min): 10% weight loss at 330° C.
DSC ($N_2$, 10° C./min): 337° C.
GPC (THF): $M_n$: 59,000 $M_w$: 180,000

B7) Poly{1-(3-[4-vinylphenoxy]-2-hydroxypropyl)-4-benzoxy-2,2,6,6-tetramethylpiperidine}

73 g (172 mmol) of the monomer from Example A7, 848 mg (5.2 mmol) of AIBN and 146 ml of toluene are introduced into a 250 ml round-bottom flask fitted with magnetic stirrer and argon balloon. The solution is freed from oxygen and stirred at 70° C. for 20 hours under argon. The polymer is precipitated in n-hexane, isolated, dissolved in THF, re-precipitated in n-hexane and dried at 60° C./0.01 mmHg, giving 29 g (40%) of a white polymer.

| Microanalysis: | C % | H % | N % |
|---|---|---|---|
| calculated | 76.56 | 8.80 | 3.31 |
| found | 75.94 | 8.77 | 2.67 |

GPC (DMF) Mn: 29,000 Mw: 42,000
TGA ($N_2$, 10° C./min): 5% weight loss at 320° C.

B8) Poly{4-(3-[4-vinylphenoxy]-2-hydroxypropoxy)-1,2,2,6,6-pentamethylpiperidine}

35 g (101 mmol) of the monomer from Example A8 and 496 mg (3 mmol) of AIBN are dissolved in 105 ml of toluene and the oxygen is removed from the solution. The mixture is stirred at 70° C. for 16 hours under argon. The polymer is then precipitated in n-hexane, dissolved in THF and re-precipitated in n-hexane. The white polymer powder is dried at 60° C./0.008 mmHg.

Yield: 17.4 g (50%)

| Microanalysis: | C % | H % | N % |
|---|---|---|---|
| calculated | 72.58 | 9.57 | 4.03 |
| found | 72.54 | 9.54 | 3.72 |

GPC (DMF): Mw: 33,000 Mn: 23,000
TGA ($N_2$, 10° C./min): 5% weight loss at 380° C.

C) USE EXAMPLES

EXAMPLE C1

Light stabilization of polypropylene fibres 2.5 g of the stabilizer according to the invention together with 1 g of Tris(2,4-di-tert-butylphenyl)phosphite, 1 g of calcium monoethyl 3,5-di-tert-butyl-4,hydroxybenzyl phosphonate, 1 g of calcium stearate and 2.5 g of $TiO_2$ (Kronos RN 57), is mixed with 1000 g of polypropylene powder (melt flow index 12 g/10 min, measured at 230° C./2.16 kg) in a turbo mixer.

The mixtures are extruded at 200–230° C. to give granules; these are subsequently converted into fibres using a pilot plant (Leonard; Sumirago/VA, Italy) under the following conditions:

Extruder temperature: 200–230° C.
Die head temperature: 255–260° C.
Stretch ratio: 1:3.5
Stretch temperature: 100° C.
Fibres: 10 den The fibres produced in this way are exposed against a white background in a Weather-O-Meter® type 65WR (Atlas Corp.) with a black panel temperature of 63° C. in accordance with ASTM D 2565-85. After various exposure times, the residual tensile strength of the samples is measured. The measurement values are used to calculate the exposure time $T_{50}$ after which the tensile strength of the samples is only half as much.

For comparative purposes, fibres containing no stabilizer according to the invention are produced and tested under otherwise identical conditions. The test results are shown in Table C1.

TABLE C1

| Exposure duration for the initial tensile strength to halve | |
|---|---|
| Stabilizer | Exposure duration |
| none | 300 h |
| from Example B1 | 1120 h |
| from Example B2b | 1030 h |
| from Example B5 | 1050 h |
| from Example B6 | 1060 h |
| from Example B8 | 1180 h |

The fibres stabilized according to the invention have excellent tenacity.

EXAMPLE C2

Stabilization of a two-coat finish

The light stabilizers are incorporated into 5–10 g of xylene and tested in a varnish of the following composition:

| | |
|---|---|
| Synthacryl ® SC 303[1] | 27.51 |
| Synthacryl ® SC 370[2] | 23.34 |
| Maprenal ® MF 650[3] | 27.29 |
| Butyl acetate/butanol (37/8) | 4.33 |
| Isobutanol | 4.87 |
| Solvesso ® 150[4] | 2.72 |
| Crystal oil K-30[5] | 8.74 |
| Flow-control agent Baysilon ® MA[6] | 1.20 |
| | 100.00 g |

[1]Acrylate resin, Hoechst AG; 65% solution in xylene/butanol 26:9
[2]Acrylate resin, Hoechst AG; 75% solution in Solvesso ® 100[4]
[3]Melamin resin, Hoechst AG; 55% solution in isobutanol
[4]Manufacturer: ESSO
[5]Manufacturer: Shell
[6]1% in Solvesso ® 150; manufacturer: Bayer AG 1% of stabilizer, based on the solids content of the finish, is added to the varnish. The comparison used is a varnish containing no light stabilizer.

The varnish is thinned with Solvesso® 100 to give a sprayable material and is sprayed onto a prepared aluminium sheet (coil coat, filler, silver-metallic basecoat) and baked at 130° C. for 30 minutes, giving a dry film thickness of 40–50 μm of varnish.

The samples are then weathered in a UVCON® exposure instrument from Atlas Corp. (UVB-313 lamps) with a cycle of UV irradiation at 60° C. for 4 hours and condensation at 50° C. for 4 hours.

The samples are examined for cracks at regular intervals. The results are shown in Table C2.

TABLE C2

| | Weathering time before cracking |
|---|---|
| Stabilizer | Cracking after |
| none | 1200 h |
| from Example B3 | 4000 h |
| from Example B4 | 4800 h |
| from Example B5 | 4800 h |
| from Example B6 | 4800 h |

The samples containing the stabilizers according to the invention have high resistance to cracking.

EXAMPLE C3

Stabilization of a photographic material 0.087 g of yellow coupler of the formula

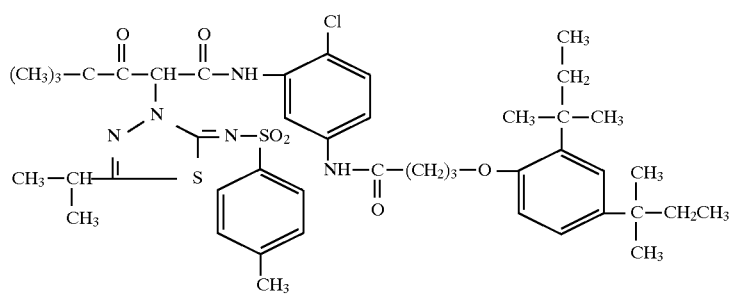

are dissolved in 2.0 ml of an ethyl acetate solution of the stabilizer according to the invention (2.25 g/100 ml). 9.0 ml of a 2.3% aqueous gelatin solution which has been adjusted to a pH of 6.5 and contains 1.744 g/l of the wetting agent of the formula

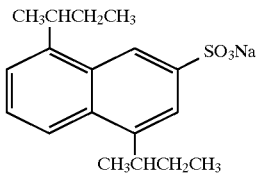

are added to 1.0 ml of this solution.

2 ml of a silver-bromide emulsion having a silver content of 6.0 g/l and 1.0 ml of a 0.7% aqueous solution of the curing agent of the formula

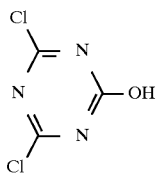

are added to 5.0 ml of the resultant coupler emulsion, and the mixture is poured onto a 13×18 cm plastic-coated paper. After a curing time of 7 days, the samples are exposed with 125 lux·s behind a silver step wedge and are subsequently processed by the Kodak Ektaprint 2® process.

The yellow wedges obtained are irradiated with a total of 60 kJ/cm$^2$ in an Atlas Weather-O-Meter by means of a 2,500 W xenon lamp behind a UV filter (Kodak 2C).

A sample without stabilizer is coated in the same way as standard.

The drop in colour density at the absorption maximum of the yellow dye, which occurs during irradiation, is measured using a Macbeth TR 924A densitometer.

The light stabilization effect is evident from the drop in colour density. The smaller the drop in density, the higher the light stabilization effectiveness.

The stabilizers according to the invention have a good light stabilization action.

EXAMPLE C4

Stabilization of polypropylene tapes 1.0 g of the stabilizer according to the invention, together with 1 g of tris(2,4-di-tert-butylphenyl)phosphite, 0.5 g of pentaerythrityl tetrakis(3-[3',5'-di-tert-butyl-4'-hydroxyphenyl]propionate) and 1 g of calcium stearate, are mixed with 1,000 g of polypropylene powder (STATOIL MF; melt flow index 4.0 g/10 min, measured at 230° C./2.16 kg) in a turbo mixer.

The mixtures are extruded at 200–230° C. to give granules; these are subsequently converted into stretch tapes with a width of 2.5 mm and a thickness of 50 μm using a pilot plant (®Leonard-Sumirago (VA), Italy) under the following conditions:

Extruder temperature: 210–230° C.
Die head temperature: 240–260° C.
Stretch ratio: 1:6

The fibres produced in this way are exposed against a white background in a Weather-O-Meter® type 65WR (Atlas Corp.) with a black panel temperature of 63° C. in accordance with ASTM D 2565-85. After various exposure times, the residual tensile strength of the samples is measured. The measurement values are used to calculate the exposure time $T_{50}$ after which the tensile strength of the samples is only half as much.

For comparative purposes, fibres containing no stabilizer according to the invention are produced and tested under otherwise identical conditions. The test results are shown in Table C4.

TABLE C4

Exposure duration for the initial tensile strength to halve

| Stabilizer | Exposure duration |
|---|---|
| none | 360 h |
| from Example B1 | 1220 h |

The sample stabilized according to the invention has excellent tenacity.

What is claimed is:

1. A compound of the formula V $$\begin{array}{c} R^4\ R^5 \\ |\ \ | \\ C=C \\ |\ \ | \\ R^6\ X \\ | \\ (C=O)_m \\ | \\ OH\ \ O \\ | \ \ / \\ E\quad N-CH_2-CH-CH_2 \\ \backslash \\ A\ \ \diagdown CH_3 \\ CH_3\ \ CH_3 \end{array}$$

(with additional $CH_3\ CH_3$ group)

in which k is 2 or 3;
m is 0 or 1;
n is 0 or 1;
A is —CH₂— or —CO—;

when A is methylene, E is $$\diagup\!\!\!\!\diagdown C \diagdown\!\!\!\!\diagup \atop R^1 \quad R^2$$

and when A is carbonyl, E is $$\diagdown N-R^{17};\atop \diagup$$

$R^1$ is hydrogen;

$R^2$ is —N($R^{13}$)$R^{14}$; $C_5$–$C_{50}$alkoxy; $C_2$–$C_{50}$alkoxy which is interrupted by a spacer selected from the group consisting of —O—, —S—, —CO—N($R^{17}$)—, —N($R^{17}$)—CO—, —NR$^{11}$—, $C_5$–$C_8$cycloalkylene and phenylene and/or contains 1 to 3 tertiary hydroxyl groups; $C_5$–$C_{12}$cycloalkoxy; $C_5$–$C_{12}$cycloalkoxy which is substituted by 1 to 4 —R$^{12}$ radicals; phenoxy; phenoxy which is substituted by 1 to 4 —R$^{12}$ radicals; or $C_7$–$C_{20}$aralkoxy, provided that $R^2$ contains 5 to 50 carbon atoms; or $R^1$ and $R^2$ together are together with the carbon atom to which they are bonded are a five- or six membered ring of the formula

[ring structures with $R^{11}$, $R^{15}$, $R^{16}$, $R^{17}$, $R^{18}$, (CH$_2$)$_k$]

or

[additional ring structure with $R^{17}$];

$R^4$ and $R^5$, independently of one another, are hydrogen; $C_1$–$C_{18}$alkyl; phenyl; or $C_7$–$C_9$phenylalkyl; or one of $R^4$ or $R^5$ is additionally chlorine;

$R^6$ has one of the meanings given for $R^4$ and $R^5$ apart from chlorine; or is a direct bond to the group X; or is a group of the formula —X—(CO)$_m$—Z$^4$ or —X—(CO)$_n$—Z$^5$;

$R^{11}$ is $C_1$–$C_{18}$alkyl; $C_5$–$C_7$cycloalkyl; phenyl; naphthyl; $C_7$–$C_9$phenylalkyl; or $C_{11}$–$C_{14}$naphthylalkyl;

$R^{12}$ is $C_1$–$C_{18}$alkyl; $C_5$–$C_7$cycloalkyl; phenyl or benzyl;

$R^{13}$ and $R^{14}$, independently of one another, are $C_1$–$C_{50}$alkyl; or $C_2$–$C_{50}$alkyl which is interrupted by a spacer selected from the group consisting of —O—, —S—, —CO—N($R^{17}$)—, —N($R^{17}$)—CO—, —NR$^{11}$—, $C_5$–$C_8$cycloalkylene and phenylene and/or contains 1 to 3 tertiary hydroxyl groups; or $C_5$–$C_{12}$cycloalkyl which is unsubstituted or substituted by 1 to 4 —$R^{12}$ radicals; phenyl which is unsubstituted or substituted by 1 to 4 —$R^{12}$ radicals; or $C_7$–$C_{20}$aralkyl; or $R^{13}$ and $R^{14}$, together with the nitrogen atom to which they are bonded, are a cyclic imide of the formula

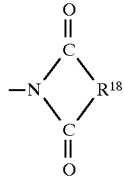

whose ring structure contains 4 to 6 carbon atoms;

$R^{15}$ and $R^{16}$, independently of one another, are H; or $C_1$–$C_{12}$alkyl; or together are straight-chain, α,ω-linked $C_4$–$C_{13}$alkylene;

$R^{17}$ is hydrogen or has one of the meanings of $R^{11}$;

$R^{18}$ is $C_2$–$C_{18}$alkylene;

X, in the case where $R^6$ is a direct bond to the group X, is the trivalent group

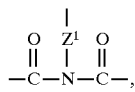

where the free valencies localized on the two carbonyl groups bond to the adjacent carbon atoms of the polymer chain;

and X, when $R^6$ is not a direct bond to the group X and in the case where m=0 or n=0, is phenylene or phenylene which is substituted by —$Z^4$ or —$Z^5$;

and X, when $R^6$ is not a direct bond to the group X and in the case where m=1 or n=1, is a direct bond; $C_1$–$C_4$alkylene; phenylene; or —$Z^2$—$Z^3$—, where $Z^2$ bonds to the carbon atom of the polymer chain;

$Z^1$ is phenylene;

$Z^2$ is —O— or phenylene;

$Z^3$ is $C_1$–$C_8$alkylene;

$Z^4$ is a group of the formula Ia

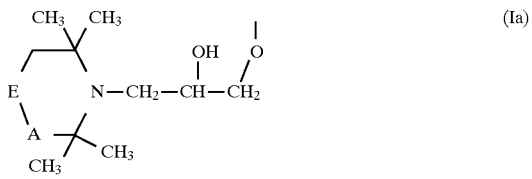

and $Z^5$ is a group of the formula IIa

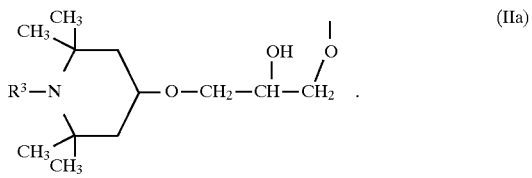

* * * * *

UNITED STATES PATENT AND TRADEMARK OFFICE
CERTIFICATE OF CORRECTION

PATENT NO. : 5,892,037
DATED : APRIL 6, 1999
INVENTOR(S) : ALFRED STEINMANN

It is certified that error appears in the above-indentified patent and that said Letters Patent is hereby corrected as shown below:

On the cover page, the Section [62] should read:

-- Related U.S. Application Data

[62] Division of Ser. No. 271,705, Jul. 7, 1994, Pat. No. 5,541,274. --.

Signed and Sealed this

Twenty-eighth Day of September, 1999

*Attest:*

Q. TODD DICKINSON

*Attesting Officer*     *Acting Commissioner of Patents and Trademarks*